(12) United States Patent
Nagaike et al.

(10) Patent No.: US 7,976,637 B2
(45) Date of Patent: Jul. 12, 2011

(54) SUBSTRATE PROCESSING SYSTEM, SUBSTRATE SURFACE PROCESSING APPARATUS, SUBSTRATE SURFACE INSPECTING APPARATUS, SUBSTRATE SURFACE INSPECTING METHOD, AND STORAGE MEDIUM STORING PROGRAM FOR IMPLEMENTING THE METHOD

(75) Inventors: Hiroshi Nagaike, Nirasaki (JP); Tsuyoshi Moriya, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 929 days.

(21) Appl. No.: 11/683,164

(22) Filed: Mar. 7, 2007

(65) Prior Publication Data

US 2007/0209591 A1    Sep. 13, 2007

Related U.S. Application Data

(60) Provisional application No. 60/788,099, filed on Apr. 3, 2006.

(30) Foreign Application Priority Data

Mar. 8, 2006   (JP) .................................. 2006-062885
Jan. 10, 2007   (JP) .................................. 2007-002603

(51) Int. Cl.
  *B08B 6/00* (2006.01)
  *C25F 1/00* (2006.01)

(52) U.S. Cl. ........................... 134/1.3; 438/745; 438/747
(58) Field of Classification Search .................. None
  See application file for complete search history.

(56) References Cited

U.S. PATENT DOCUMENTS 4,661,369 A * 4/1987 Crane ................................ 427/8
4,897,676 A * 1/1990 Sedberry ....................... 347/148

FOREIGN PATENT DOCUMENTS

JP           1-219546         9/1989

* cited by examiner

*Primary Examiner* — Duy-Vu N Deo
(74) *Attorney, Agent, or Firm* — Oblon, Spivak, McClelland, Maier & Neustadt, L.L.P.

(57) ABSTRACT

A substrate processing system which enables a minute pieces of foreign matter attached to a substrate surface to be detected and are suitable for mass production of substrates. The substrate processing system has a substrate processing apparatus that carries out predetermined processing on a substrate. The substrate processing system comprises a substrate surface processing apparatus having a fluid supply unit that supplies onto a surface of the substrate a fluid containing an altering substance that alters a substance exposed at the surface of the substrate, and a substrate surface inspecting apparatus that inspects the surface of the substrate onto which the fluid has been supplied.

6 Claims, 11 Drawing Sheets

SUBSTRATE PROCESSING SYSTEM, SUBSTRATE SURFACE PROCESSING APPARATUS, SUBSTRATE SURFACE INSPECTING APPARATUS, SUBSTRATE SURFACE INSPECTING METHOD, AND STORAGE MEDIUM STORING PROGRAM FOR IMPLEMENTING THE METHOD

BACKGROUND OF THE INVENTION

1. Field of the Invention

The present invention relates to a substrate processing system, a substrate surface processing apparatus, a substrate surface inspecting apparatus, a substrate surface inspecting method, and a storage medium storing a program for implementing the method, and more particularly relates to a substrate processing system and a substrate processing method according to which a substrate surface having foreign matter attached thereto can be inspected.

2. Description of the Related Art

A substrate processing system that carries out plasma processing on wafers as substrates has a processing module that houses a wafer and carries out the plasma processing, a load lock module that transfers each wafer into the processing module, and a loader module that takes out each wafer from a container housing a plurality of the wafers and transfers the wafer into and out of the load lock module. In such a substrate processing system, foreign matter such as particles or grease may become attached to a surface of a wafer when the wafer is transferred. Such foreign matter attached to the surface of a wafer causes defects in semiconductor devices manufactured from the wafer, for example short-circuiting of wiring, and hence must be removed.

The width and so on of wiring grooves in semiconductor devices is becoming smaller year by year. To cope with this, the target value for the size of foreign matter to be detected is stipulated by the ITRS (International Technology Roadmap for Semiconductors) as shown by the roadmap shown in Table 1 below.

TABLE 1

| | Year of Production | | | | | |
|---|---|---|---|---|---|---|
| | 2004 | 2005 | 2006 | 2007 | 2008 | 2009 |
| Critical foreign matter size (nm) | 45 | 40 | 35 | 33 | 29 | 25 |

According to the above roadmap, foreign matter of size 29 mm must be detectable by 2008.

Substrate surface inspecting apparatuses that use a scattered laser light method have been known from hitherto as apparatuses for detecting the size of particles attached to the surface of a wafer. Such a substrate surface inspecting apparatus has an inspection stage on which the wafer is mounted and rotated, a laser beam irradiating unit that irradiates a laser beam onto the surface of the rotating wafer, a light receiver that receives some of scattered light scattered from the surface irradiated by the laser beam, and a photoelectric converter that converts an optical signal from the light receiver into an electrical signal. In the case that a particle is attached to the surface of the wafer, upon the particle being irradiated by the laser beam, the magnitude of the scattered light changes in accordance with the size of the particle. Such a substrate surface inspecting apparatus detects the size and number of particles attached to the surface of the wafer based on the voltage of the electrical signal produced through the conversion by the photoelectric converter and the number of such signals (see, for example, Japanese Laid-open Patent Publication (Kokai) No. H01-219546).

However, the size of particles that can be detected by such a substrate surface inspecting apparatus using the scattered laser light method is determined by the resolution of the photoelectric converter. The resolution of current photoelectric converters is 50 to 70 nm at best, and hence such a substrate surface inspecting apparatus cannot detect particles of the 2004 critical foreign matter size stipulated in the above roadmap.

As a substrate surface inspecting apparatus capable of detecting particles of size approximately 30 nm, there is known a substrate surface inspecting apparatus that scans the surface of a wafer using an EB (electron beam), and examines the surface with an SEM (scanning electron microscope); however, such a substrate surface inspecting apparatus can only inspect a few wafers per day, and hence is not suitable for mass production of wafers.

That is, at present there is no substrate surface inspecting apparatus that is capable of detecting particles of size approximately 30 nm and is suitable for mass production of wafers.

SUMMARY OF THE INVENTION

It is an object of the present invention to provide a substrate processing system, a substrate surface processing apparatus, a substrate surface inspecting apparatus, a substrate surface inspecting method, and a storage medium storing a program for implementing the method, which enable minute pieces of foreign matter attached to a substrate surface to be detected and are suitable for mass production of substrates.

To attain the above object, in a first aspect of the present invention, there is provided a substrate processing system having a substrate processing apparatus that carries out predetermined processing on a substrate, the substrate processing system comprising: a substrate surface processing apparatus having a fluid supply unit that supplies onto a surface of the substrate a fluid containing an altering substance that alters a substance exposed at the surface of the substrate; and a substrate surface inspecting apparatus that inspects the surface of the substrate onto which the fluid has been supplied.

According to the first aspect of the present invention, a fluid containing an altering substance that alters a substance exposed at the surface of the substrate is supplied onto the surface of the substrate, and the surface of the substrate onto which the fluid has been supplied is inspected. In the case that a minute piece of foreign matter is attached to the surface of the substrate, the fluid is trapped between the foreign matter and the surface of the substrate, and the altering substance in the fluid alters the substance exposed at the surface of the substrate. As a result, alteration marks are formed around the piece of foreign matter, the marks being larger in size than the piece of foreign matter, and hence the marks can easily be detected. By detecting the alteration marks, a minute piece of foreign matter attached to the surface of the substrate can thus be detected using a method suitable for mass production of substrates, there being no need to examine the surface of the substrate with an SEM.

Preferably, the substrate surface processing apparatus has a housing chamber that houses the substrate, and a pressure reducing unit that reduces a pressure in the housing chamber.

According to the first aspect of the present invention, the pressure in the housing chamber in which the substrate is housed is reduced. The fluid trapped between a piece of foreign matter and the surface of the substrate thus freezes due to adiabatic expansion, and hence stays around the foreign matter reliably. As a result, alteration marks can be formed around the foreign matter reliably. A minute piece of foreign matter attached to the surface of the substrate can thus be detected yet more easily.

Preferably, the altering substance corrodes the exposed substance.

According to the first aspect of the present invention, the altering substance corrodes the exposed substance. As a result, alteration marks can be formed around a piece of foreign matter yet more reliably.

More preferably, the altering substance is an acid, an alkali, a substance that combines with another substance to form an acid, or a substance that combines with another substance to form an alkali.

According to the first aspect of the present invention, the altering substance is an acid, an alkali, a substance that combines with another substance to form an acid, or a substance that combines with another substance to form an alkali. As a result, the altering substance can easily corrode the exposed substance.

Preferably, the substrate surface inspecting apparatus has a stage on which the substrate is mounted and which rotates the mounted substrate, a laser beam irradiating unit that irradiates a laser beam onto the surface of the substrate, a light receiver that receives at least some of scattered light scattered from the surface, and a photoelectric converter the converts the scattered light received by the light receiver into an electrical signal.

According to the first aspect of the present invention, the substrate is rotated, a laser beam is irradiated onto the surface of the substrate, and at least some of the scattered light scattered from the surface is converted into an electrical signal. As a result, a minute piece of foreign matter around which alteration marks have been formed can be detected efficiently.

Preferably, the substrate surface inspecting apparatus has a stage on which the substrate is mounted and which rotates the mounted substrate, an EB irradiating unit that irradiates an EB onto the surface of the substrate, and a current measuring unit that is connected to the stage and measures a current produced due to the EB irradiated onto the surface of the substrate.

According to the first aspect of the present invention, the surface of the substrate is irradiated by an EB, and a current produced due to the EB irradiated onto the surface of the substrate is measured. A piece of foreign matter attached to the surface of the substrate and alteration marks formed around the foreign matter capture electrons, and hence upon any of the foreign matter and the alteration marks being irradiated by the EB, the value of the current decreases. A minute piece of foreign matter having alteration marks formed therearound can thus be detected accurately. Moreover, because the minute piece of foreign matter can be detected merely by measuring the current, the piece of foreign matter can be detected more efficiently.

Preferably, the substrate surface inspecting apparatus has an EB irradiating unit that irradiates EBs over a predetermined region of the surface of the substrate, and a charge measuring unit that measures a charge distribution over the predetermined region.

According to the first aspect of the present invention, EBs are irradiated over a predetermined region of the surface of the substrate, and the charge distribution over the predetermined region is measured. A piece of foreign matter attached to the surface of the substrate and alteration marks capture electrons, and hence the charge increases at the location of any of the piece of foreign matter and the alteration marks. A piece of foreign matter having alteration marks formed therearound can thus be detected accurately by measuring the charge distribution over the surface. Moreover, because the minute piece of foreign matter can be detected merely by measuring the charge distribution, the piece of foreign matter can be detected more efficiently.

To attain the above object, in a second aspect of the present invention, there is provided a substrate surface processing apparatus comprising a fluid supply unit that supplies onto a surface of a substrate, the surface of which is to be inspected, a fluid containing an altering substance that alters a substance exposed at the surface of the substrate.

To attain the above object, in a third aspect of the present invention, there is provided a substrate surface inspecting apparatus that inspects a surface of a substrate, the substrate surface inspecting apparatus comprising: a fluid supply unit that supplies onto the surface of the substrate a fluid containing an altering substance that alters a substance exposed at the surface of the substrate.

To attain the above object, in a fourth aspect of the present invention, there is provided a substrate processing system having a substrate processing apparatus that carries out predetermined processing on a substrate, the substrate processing system comprising: a substrate surface processing apparatus having an etching unit that etches a surface of the substrate; and a substrate surface inspecting apparatus that inspects the surface of the substrate of which the surface has been etched.

According to the fourth aspect of the present invention, the surface of the substrate is etched, and the etched surface of the substrate is inspected. In the case that a minute piece of foreign matter is attached to the surface of the substrate, upon the surface being etched, the foreign matter acts as a micromask, and hence the substance below the foreign matter is not etched. That is, a projection having the piece of foreign matter on top thereof is formed on the surface of the substrate. The projection scatters a laser beam well, and thus can easily be detected. A minute piece of foreign matter attached to the surface of the substrate can thus be detected using a method suitable for mass production of substrates, there being no need to examine the surface of the substrate with an SEM.

To attain the above object, in a fifth aspect of the present invention, there is provided a substrate processing system having a substrate processing apparatus that carries out predetermined processing on a substrate, the substrate processing system comprising: a substrate surface processing apparatus having an exposing unit that exposes to light a positive type photosensitive substance that has been applied onto a surface of the substrate, and a developing unit that develops the exposed photosensitive substance; and a substrate surface inspecting apparatus that inspects the surface of the substrate on which the photosensitive substance has been developed.

According to the fifth aspect of the present invention, a positive type photosensitive substance that has been applied onto the surface of the substrate is exposed to light, the exposed photosensitive substance is developed, and the surface of the substrate on which the photosensitive substance has been developed is inspected. In the case that a minute piece of foreign matter is attached to the surface of the substrate onto the surface of which has been applied the photosensitive substance, upon the surface being exposed, the foreign matter acts as a mask, and hence the photosensitive substance is not exposed below the foreign matter, and thus is not altered through photochemical reaction. That is, below the foreign matter, the photosensitive substance is not dissolved in the developing, and as a result a hill-like projection having the piece of foreign matter on top thereof is formed on the surface of the substrate. The projection scatters a laser beam well, and thus can easily be detected. A minute piece of foreign matter attached to the surface of the substrate can thus be detected using a method suitable for mass production of substrates, there being no need to examine the surface of the substrate with an SEM.

To attain the above object, in a sixth aspect of the present invention, there is provided a substrate surface inspecting method for a substrate processing system having a substrate processing apparatus that carries out predetermined processing on a substrate, the substrate surface inspecting method comprising: a fluid supply step of supplying onto a surface of the substrate a fluid containing an altering substance that alters a substance exposed at the surface of the substrate and a substrate surface inspecting step of inspecting the surface of the substrate onto which the fluid has been supplied.

Preferably, a substrate surface inspecting method as claimed in claim 1, further having a substrate leaving step of, after the fluid has been supplied onto the surface of the substrate, leaving the substrate for a predetermined time period.

According to the sixth aspect of the present invention, after the fluid has been supplied onto the surface of the substrate, the substrate is left for a predetermined time period. While the substrate is being left, the altering substance in the fluid sufficiently alters the substance exposed at the surface of the substrate. As a result, alteration marks can be formed around a piece of foreign matter reliably. A minute piece of foreign matter can thus be detected yet more easily.

To attain the above object, in a seventh aspect of the present invention, there is provided a substrate surface inspecting method for a substrate processing system having a substrate processing apparatus that carries out predetermined processing on a substrate, the substrate surface inspecting method comprising: a surface etching step of etching a surface of the substrate; and a substrate surface inspecting step of inspecting the surface of the substrate of which the surface has been etched.

To attain the above object, in an eighth aspect of the present invention, there is provided a substrate surface inspecting method for a substrate processing system having a substrate processing apparatus that carries out predetermined processing on a substrate, the substrate surface inspecting method comprising: an exposing step of exposing to light a photosensitive substance that has been applied onto a surface of the substrate; a developing step of developing the exposed photosensitive substance; and a substrate surface inspecting step of inspecting the surface of the substrate on which the photosensitive substance has been developed.

To attain the above object, in a ninth aspect of the present invention, there is provided a computer-readable storage medium storing a program for causing a computer to implement a substrate surface inspecting method for a substrate processing system having a substrate processing apparatus that carries out predetermined processing on a substrate, the program comprising: a fluid supply module for supplying onto a surface of the substrate a fluid containing an altering substance that alters a substance exposed at the surface of the substrate; and a substrate surface inspecting module for inspecting the surface of the substrate onto which the fluid has been supplied.

To attain the above object, in a tenth aspect of the present invention, there is provided a computer-readable storage medium storing a program for causing a computer to implement a substrate surface inspecting method for a substrate processing system having a substrate processing apparatus that carries out predetermined processing on a substrate, the program comprising: a surface etching module for etching a surface of the substrate; and a substrate surface inspecting module for inspecting the surface of the substrate of which the surface has been etched.

To attain the above object, in an eleventh aspect of the present invention, there is provided a computer-readable storage medium storing a program for causing a computer to implement a substrate surface inspecting method for a substrate processing system having a substrate processing apparatus that carries out predetermined processing on a substrate, the program comprising: an exposing module for exposing to light a photosensitive substance that has been applied onto a surface of the substrate; a developing module for developing the exposed photosensitive substance; and a substrate surface inspecting module for inspecting the surface of the substrate on which the photosensitive substance has been developed.

To attain the above object, in a twelfth aspect of the present invention, there is provided a substrate processing system having a substrate processing apparatus that carries out predetermined processing on a substrate, the substrate processing system comprising: a substrate surface processing apparatus having a housing chamber that houses the substrate, a pressure reducing unit that reduces a pressure in the housing chamber, and a fluid supply unit that supplies onto a surface of the substrate a fluid containing a reactive substance that reacts with water to form a solid; and a substrate surface inspecting apparatus that inspects the surface of the substrate onto which the fluid has been supplied.

According to the twelfth aspect of the present invention, the pressure in the housing chamber in which the substrate is housed is reduced, a fluid containing a reactive substance that reacts with water to form a solid is supplied onto the surface of the substrate, and the surface of the substrate onto which the fluid has been supplied is inspected. In the case that a minute piece of foreign matter is attached to the surface of the substrate, water is trapped between the foreign matter and the surface of the substrate, the trapped water freezes due to adiabatic expansion, and the frozen water grows in a snow crystal shape around the foreign matter. The water that has grown in a snow crystal shape reacts with the supplied fluid to form a solid. As a result, the solid is formed in a snow crystal shape around the piece of foreign matter, the solid being larger in size than the piece of foreign matter, and hence the solid can easily be detected. By detecting the snow crystal-shaped solid, a minute piece of foreign matter attached to the surface of the substrate can thus be detected using a method suitable for mass production of substrates, there being no need to examine the surface of the substrate with an SEM.

To attain the above object, in a thirteenth aspect of the present invention, there is provided a substrate processing system having a substrate processing apparatus that carries out predetermined processing on a substrate, the substrate processing system comprising: a substrate surface processing apparatus having a stage on which the substrate is mounted and which rapidly cools the mounted substrate, and a fluid supply unit that supplies onto a surface of the substrate a fluid containing a reactive substance that reacts with water to form a solid; and a substrate surface inspecting apparatus that inspects the surface of the substrate onto which the fluid has been supplied.

According to the thirteenth aspect of the present invention, the substrate is rapidly cooled, a fluid containing a reactive substance that reacts with water to form a solid is supplied onto the surface of the substrate, and the surface of the substrate onto which the fluid has been supplied is inspected. In the case that a minute piece of foreign matter is attached to the surface of the substrate, supercooled water produced through the substrate being rapidly cooled collects and freezes around the foreign matter, and the frozen water grows in a snow crystal shape around the foreign matter. The water that has grown in a snow crystal shape reacts with the supplied fluid to form a solid. As a result, the solid is formed in a snow crystal shape around the piece of foreign matter, the solid being larger in size than the piece of foreign matter, and hence the solid can easily be detected. By detecting the snow crystal-shaped solid, a minute piece of foreign matter attached to the surface of the substrate can thus be detected using a method suitable for mass production of substrates, there being no need to examine the surface of the substrate with an SEM.

Preferably, the reactive substance is a cyanoacrylate. Such a cyanoacrylate reacts with water, polymerizing and hardening to become a polycyanoacrylate. The polycyanoacrylate will not evaporate upon releasing to atmospheric pressure. The polycyanoacrylate can thus be made to remain reliably as a solid around a piece of foreign matter.

Preferably, the stage rapidly cools the substrate to a temperature of not more than 0° C.

According to the thirteenth aspect of the present invention, the substrate is rapidly cooled to a temperature of not more than 0° C. Water in the atmosphere above the surface of the substrate can thus be put into a supercooled state reliably, and hence supercooled water can be reliably produced on the surface of the substrate.

To attain the above object, in a fourteenth aspect of the present invention, there is provided a substrate surface processing apparatus comprising a housing chamber that houses a substrate a surface of which is to be inspected, a pressure reducing unit that reduces a pressure in the housing chamber, and a fluid supply unit that supplies onto the surface of the substrate a fluid containing a reactive substance that reacts with water to form a solid.

According to the fourteenth aspect of the present invention, the pressure in the housing chamber in which the substrate is housed is reduced, a fluid containing a reactive substance that reacts with water to form a solid is supplied onto the surface of the substrate. In the case that a minute piece of foreign matter is attached to the surface of the substrate, water is trapped between the foreign matter and the surface of the substrate, the trapped water freezes due to adiabatic expansion, and the frozen water grows in a snow crystal shape around the foreign matter. The water that has grown in a snow crystal shape reacts with the supplied fluid to form a solid. As a result, the solid is formed in a snow crystal shape around the piece of foreign matter, the solid being larger in size than the piece of foreign matter, and hence the solid can easily be detected. By detecting the snow crystal-shaped solid, a minute piece of foreign matter attached to the surface of the substrate can thus be detected using a method suitable for mass production of substrates, there being no need to examine the surface of the substrate with an SEM.

To attain the above object, in a fifteenth aspect of the present invention, there is provided a substrate surface processing apparatus comprising a stage on which is mounted a substrate a surface of which is to be inspected and which rapidly cools the mounted substrate, and a fluid supply unit that supplies onto the surface of the substrate a fluid containing a reactive substance that reacts with water to form a solid.

To attain the above object, in a sixteenth aspect of the present invention, there is provided a substrate surface inspecting method for a substrate processing system having a substrate processing apparatus that carries out predetermined processing on a substrate, the substrate surface inspecting method comprising: a pressure reducing step of reducing a pressure in a housing chamber housing the substrate; a fluid supply step of supplying onto a surface of the substrate a fluid containing a reactive substance that reacts with water to form a solid; and a substrate surface inspecting step of inspecting the surface of the substrate onto which the fluid has been supplied.

To attain the above object, in a seventeenth aspect of the present invention, there is provided a substrate surface inspecting method for a substrate processing system having a substrate processing apparatus that carries out predetermined processing on a substrate, the substrate surface inspecting method comprising: a rapid cooling step of rapidly cooling the substrate; a fluid supply step of supplying onto a surface of the substrate a fluid containing a reactive substance that reacts with water to form a solid; and a substrate surface inspecting step of inspecting the surface of the substrate onto which the fluid has been supplied.

To attain the above object, in an eighteenth aspect of the present invention, there is provided a computer-readable storage medium storing a program for causing a computer to implement a substrate surface inspecting method for a substrate processing system having a substrate processing apparatus that carries out predetermined processing on a substrate, the program comprising: a pressure reducing module for reducing a pressure in a housing chamber housing the substrate; a fluid supply module for supplying onto a surface of the substrate a fluid containing a reactive substance that reacts with water to form a solid; and a substrate surface inspecting module for inspecting the surface of the substrate onto which the fluid has been supplied.

To attain the above object, in a nineteenth aspect of the present invention, there is provided a computer-readable storage medium storing a program for causing a computer to implement a substrate surface inspecting method for a substrate processing system having a substrate processing apparatus that carries out predetermined processing on a substrate, the program comprising: a rapid cooling module for rapidly cooling the substrate; a fluid supply module for supplying onto a surface of the substrate a fluid containing a reactive substance that reacts with water to form a solid; and a substrate surface inspecting module for inspecting the surface of the substrate onto which the fluid has been supplied.

The above and other objects, features, and advantages of the invention will become more apparent from the following detailed description taken in conjunction with the accompanying drawings.

DETAILED DESCRIPTION OF THE PREFERRED EMBODIMENTS

Embodiments of the present invention will now be described with reference to the drawings.

First, a substrate processing system according to a first embodiment of the present invention will be described.

Figure 1:
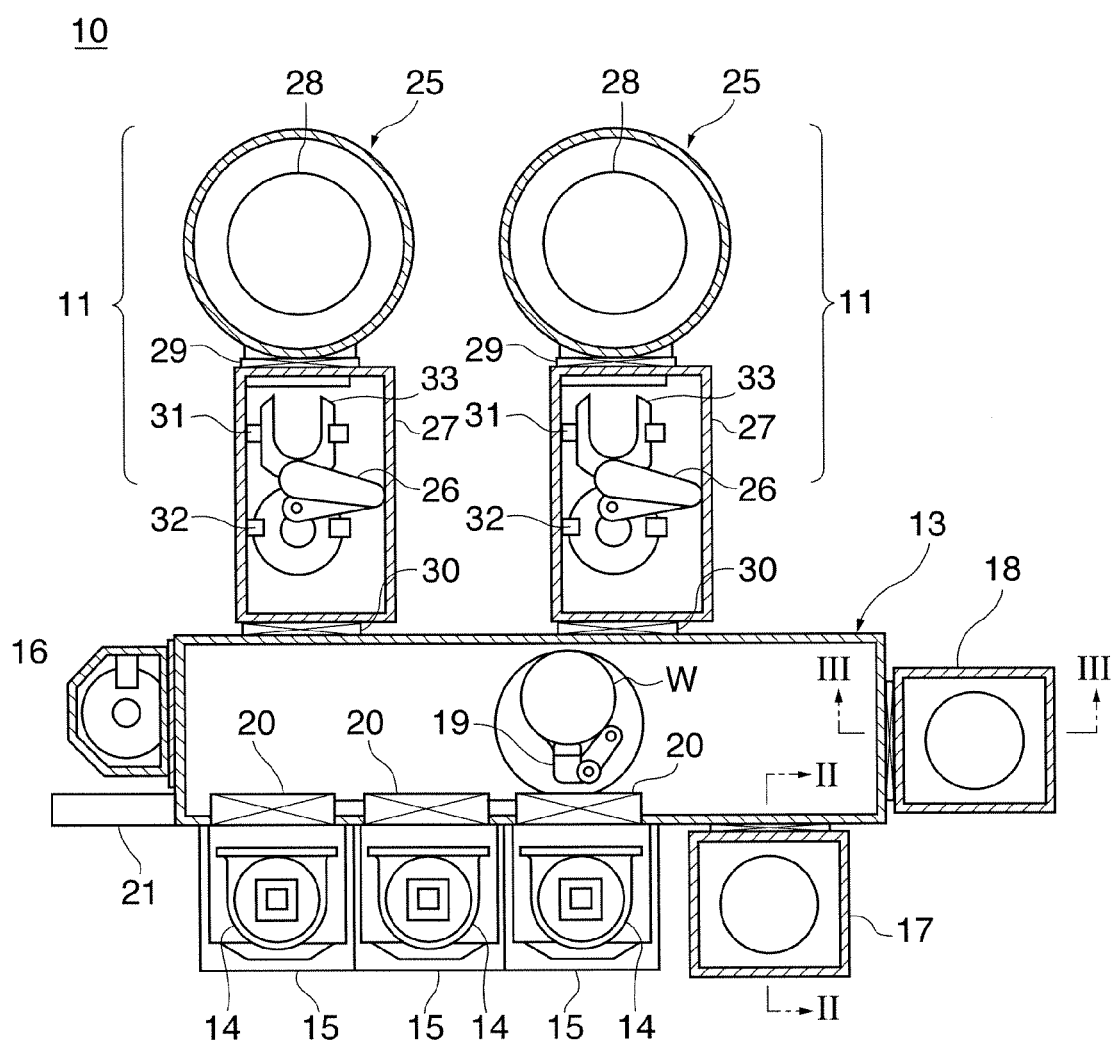
FIG. 1 is a plan view schematically showing the construction of a substrate processing system according to a first embodiment of the present invention.

FIG. 1 is a plan view schematically showing the construction of the substrate processing system according to the first embodiment of the present invention.

As shown in FIG. 1, the substrate processing system 10 is comprised of two process ships 11 for carrying out reactive ion etching (hereinafter referred to as "RIE") processing or the like on semiconductor device wafers (hereinafter referred to merely as "wafers") W, and a loader module 13, which is a rectangular common transfer chamber to which each of the two process ships 11 is connected.

In addition to the process ships 11, the loader module 13 has connected thereto, at least one, for example one to five (in FIG. 1, three) FOUP mounting stage(s) 15 on each of which is mounted a FOUP (front opening unified pod) 14, which is a container housing twenty-five of the wafers W, an orienter 16 that carries out pre-alignment of the position of each wafer W transferred out from a FOUP 14, a surface processing apparatus 17, and a surface inspecting apparatus 18.

The two process ships 11 are connected to a side wall of the loader module 13 in a longitudinal direction of the loader module 13, disposed facing the three FOUP mounting stages 15 with the loader module 13 therebetween. The orienter 16 is disposed at one end of the loader module 13 in the longitudinal direction of the loader module 13. The surface inspecting apparatus 18 is disposed at the other end of the loader module 13 in the longitudinal direction of the loader module 13. The surface processing apparatus 17 is disposed alongside the three FOUP mounting stages 15.

A scalar-type dual arm transfer arm mechanism 19 for transferring the wafers W is disposed inside the loader module 13, and at least one, for example one to five (in FIG. 1, three) loading port(s) 20 through which the wafers W are introduced into the loader module 13 is/are disposed in a side wall of the loader module 13 in correspondence with the FOUP mounting stage(s) 15. The transfer arm mechanism 19 takes a wafer W out from a FOUP 14 mounted on a FOUP mounting stage 15 through the corresponding loading port 20, and transfers the removed wafer W into and out of the process ships 11, the orienter 16, the surface processing apparatus 17, and the surface inspecting apparatus 18.

Each of the process ships 11 has a processing module 25 (substrate processing apparatus) as a plasma processing chamber in which the RIE processing is carried out on each wafer W, and a load lock module 27 containing a link-type single pick-type transfer arm 26 for transferring each wafer W into and out of the processing module 25.

The processing module 25 has a cylindrical processing chamber, and an upper electrode and a lower electrode disposed in the chamber. The distance between the upper electrode and the lower electrode is set to an appropriate value for carrying out the RIE processing on each wafer W. Moreover, the lower electrode has in a top portion thereof an ESC 28 for chucking the wafer W thereto using a Coulomb force or the like.

In the processing module 25, a processing gas, for example a gas comprised of $CF_4$ gas and argon gas, is introduced into the chamber and an electric field is generated between the upper electrode and the lower electrode, whereby the introduced processing gas is turned into plasma so as to produce ions and radicals. The wafer W is subjected to the RIE processing by the ions and radicals.

In each process ship 11, the internal pressure of the processing module 25 is held at vacuum, whereas the internal pressure of the loader module 13 is held at atmospheric pressure. The load lock module 27 is thus provided with a vacuum gate valve 29 in a connecting part between the load lock module 27 and the processing module 25, and an atmospheric gate valve 30 in a connecting part between the load lock module 27 and the loader module 13, whereby the load lock module 27 is constructed as a preliminary vacuum transfer chamber whose internal pressure can be adjusted.

Within the load lock module 27, the transfer arm 26 is disposed in an approximately central portion of the load lock module 27; first buffers 31 are disposed toward the processing module 25 with respect to the transfer arm 26, and second buffers 32 are disposed toward the loader module 13 with respect to the transfer arm 26. The first buffers 31 and the second buffers 32 are disposed above a track along which a supporting portion (pick) 33 moves, the supporting portion 33 being disposed at a distal end of the transfer arm 26 and being for supporting each wafer W. After having being subjected to the RIE processing, each wafer W is temporarily laid by above the track of the supporting portion 33, whereby swapping over of the wafer W that has been subjected to the RIE processing and a wafer W yet to be subjected to the RIE processing can be carried out smoothly in the processing module 25.

Moreover, the substrate processing apparatus 10 has a system controller (not shown) for controlling operations of the process ships 11, the loader module 13, the orienter 16, the surface processing apparatus 17, and the surface inspecting apparatus 18 (hereinafter referred to collectively as "component elements"), and an operation panel 21 that is disposed at one end of the loader module 13 in the longitudinal direction of the loader module 13.

The system controller controls the operations of the component elements in accordance with a recipe, which is a program for the RIE processing. The operation panel 21 has a display section (not shown) comprised of, for example, an LCD (liquid crystal display), for displaying the state of operation of the component elements.

Figure 2:
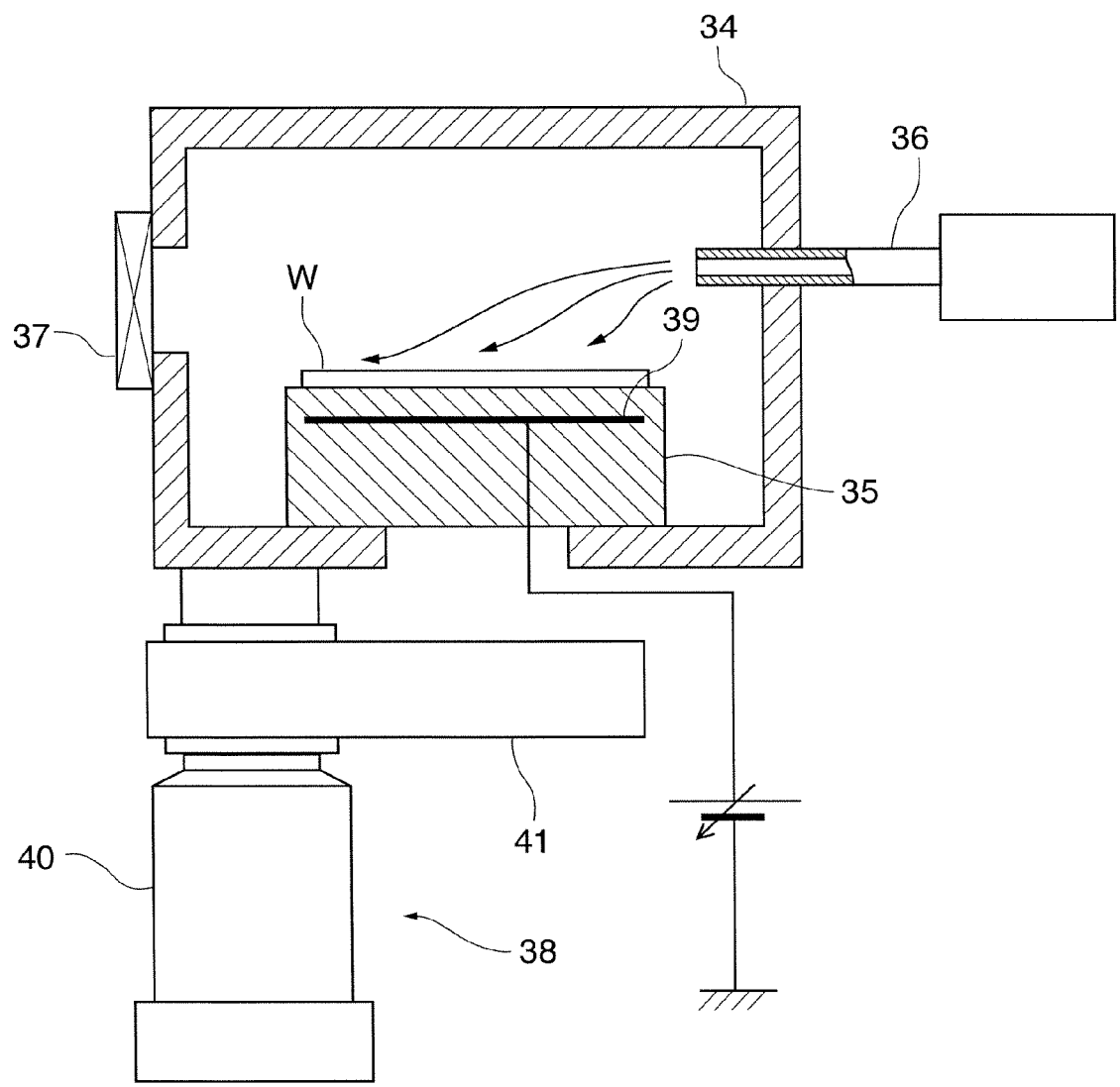
FIG. 2 is a sectional view taken along line II-II in FIG. 1.

FIG. 2 is a sectional view taken along line II-II in FIG. 1. A direction that is upward in FIG. 2 will be referred to as "above" or "upper", and a direction that is downward in FIG. 2 as "below" or "lower".

As shown in FIG. 2, the surface processing apparatus 17 is comprised of a box-shaped housing chamber 34, a wafer stage 35 that is disposed in a lower portion of the housing chamber 34 and on which a wafer W is mounted, a fluid supply unit 36 that is disposed in an upper portion of the housing chamber 34 and supplies a predetermined fluid, for example a fluorine-containing gas, into the housing chamber 34, an openable/closable gate valve 37 that is disposed in a side of the housing chamber 34, and an exhaust unit 38 (pressure reducing unit) that exhausts the fluid out from the housing chamber 34. The surface processing apparatus 17 is connected to the loader module 13 via the gate valve 37, the interior of the housing chamber 34 being communicated with the interior of the loader module 13 when the gate valve 37 is open.

The wafer stage 35 contains a heater 39 comprised of a heating wire or the like disposed below a wafer W mounting surface, whereby the wafer stage 35 heats the mounted wafer W to a desired temperature. The exhaust unit 38 has a TMP (Turbo Molecular Pump) 40 for exhausting gas out from the housing chamber 34, a DP (dry pump) (not shown) disposed below the TMP 40, and an APC (Adaptive Pressure Control) valve 41 which is a variable butterfly valve disposed between the housing chamber 34 and the TMP 40. The APC valve 41 is used for setting the pressure in the housing chamber 34 to a desired pressure. The pressure in the housing chamber 34 is reduced down to a substantially vacuum state by the exhaust unit 38.

The surface processing apparatus 17 carries out pre-inspection surface processing, described below, on each wafer W which has been transferred through at least the loader module 13. In the pre-inspection surface processing, the wafer W may be cooled rather than heated so as to selectively adsorb gas around a particle, and hence the wafer stage 35 may contain not only the heater 39, but also a cooling mechanism, for example a coolant circulating path, for cooling the wafer W.

Figure 3:
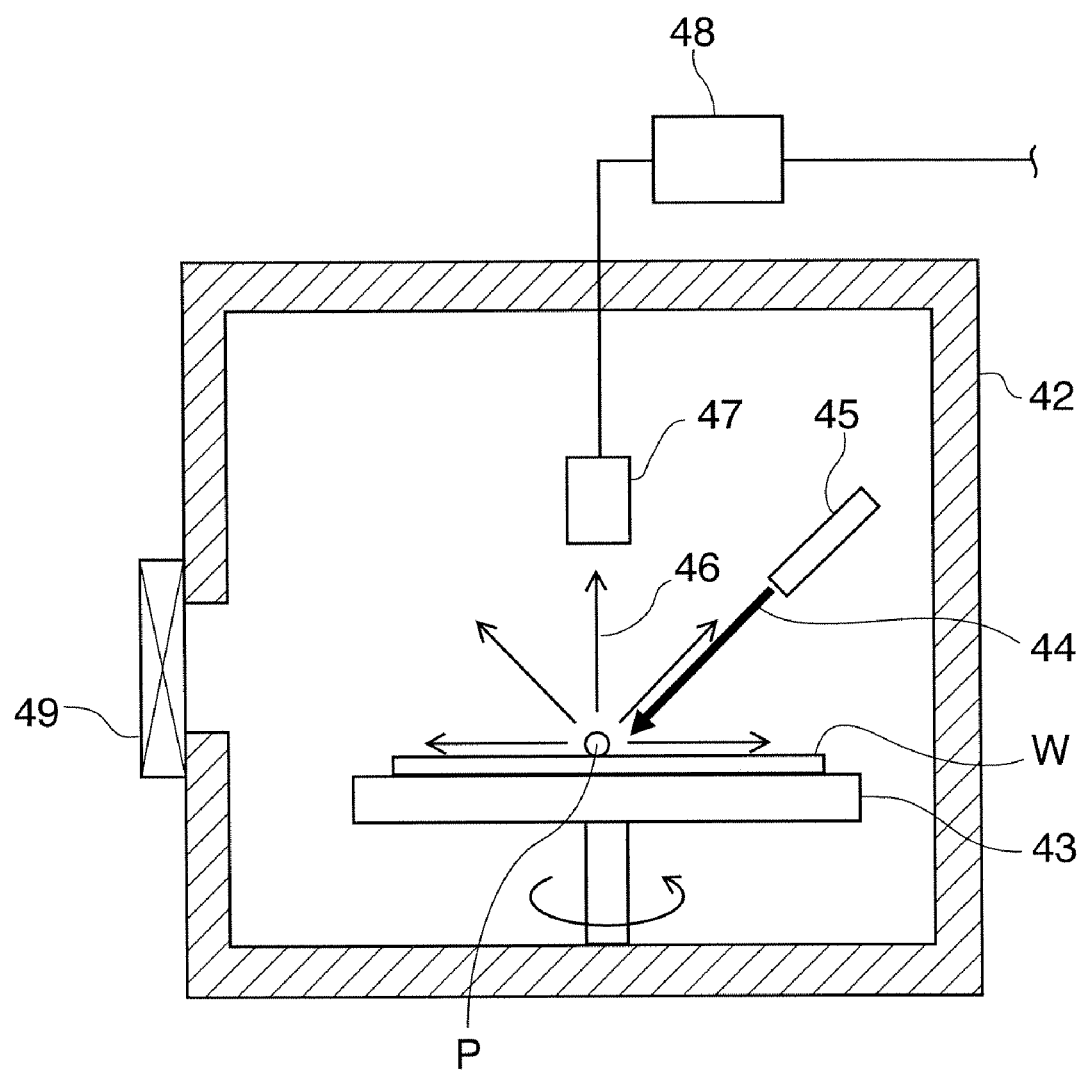
FIG. 3 is a sectional view taken along line III-III in FIG. 1.

FIG. 3 is a sectional view taken along line III-III in FIG. 1. A direction that is upward in FIG. 3 will be referred to as "above" or "upper", and a direction that is downward in FIG. 3 as "below" or "lower".

As shown in FIG. 3, the surface inspecting apparatus 18 is comprised of a box-shaped housing chamber 42, a wafer stage 43 (stage) that is disposed in a lower portion of the housing chamber 42 and on which a wafer W is mounted and rotated, a laser beam irradiating unit 45 that irradiates a laser beam 44 onto a surface of the rotating wafer W, a light receiver 47 (collimator) that receives some of scattered light 46 scattered from the surface irradiated by the laser beam 44, a photoelectric converter (photomultiplier) 48 that converts the scattered light received by the light receiver 47 into an electrical signal, and an openable/closable gate valve 49 that is disposed in a side of the housing chamber 42. The photoelectric converter 48 is connected to the system controller.

The surface inspecting apparatus 18 is connected to the loader module 13 via the gate valve 49, the interior of the housing chamber 42 being communicated with the interior of the loader module 13 when the gate valve 49 is open.

In the surface inspecting apparatus 18, in the case that a particle P is attached to the surface of the wafer W mounted on the wafer stage 43, upon the particle P being irradiated by the laser beam 44, scattered light 46 arises. Some of the scattered light 46 is received by the light receiver 47, and further converted into an electrical signal by the photoelectric converter 48, the electrical signal being sent to the system controller. The magnitude of the scattered light 46 changes in accordance with the size of the particle P, and hence the system controller detects the size of the particle P based on a voltage of the electrical signal, which corresponds to the magnitude of the scattered light 46.

Prior to the present invention, the present inventors discovered that, of wafers transferred through the loader module of the substrate processing system, a snow crystal-shaped pattern or amoeba-shaped pattern is seen here and there on the surface of several wafers. It was found that there is a minute piece of foreign matter such as a particle or piece of grease of size approximately 300 nm at the center of the pattern, and the size of the pattern is approximately 20 µm.

Moreover, the present inventors investigated the transfer history of wafers on which such a pattern arose and wafers on which such a pattern did not arise, and found that such a pattern does not arise on the surface of a wafer in the case that the wafer has been transferred into a load lock module but the vacuum gate valve remained closed so that the load lock module was not communicated with the processing chamber of the corresponding processing module. Moreover, the present inventors found that such a pattern does arise on the surface of a wafer in the case that the wafer is transferred into the load lock module and the vacuum gate valve is opened and closed so that the load lock module is communicated with the processing chamber of the corresponding processing module. It was thus inferred that the arising of such a pattern is related to gas in the processing chamber.

Moreover, it was found that upon such a pattern that has arisen on the surface of a wafer being irradiated with an EB, the pattern disappears. That is, the pattern disappears upon being irradiated at a very low energy, and hence it was inferred that the pattern arises through alteration, for example corrosion, of only a surface-most portion of the wafer. Furthermore, many of the patterns are snow crystal-shaped, and hence it was inferred that the arising of the patterns is related to freezing of water.

As a result of the above observations and findings, the present inventors hypothesized the following as the mechanism by which a pattern arises on the surface of a wafer.

Figure 4A:
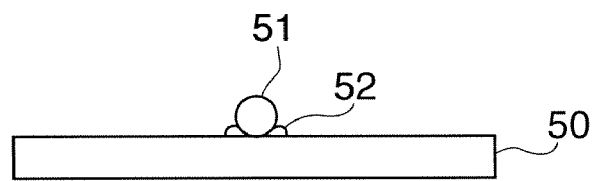
FIGS. 4A to 4D are views for explaining a mechanism by which a pattern arises on a wafer surface.

(1) When the wafer 50 is transferred through the loader module, or transferred into a load lock module which is open to atmospheric pressure, a particle 51 becomes attached to the surface of the wafer 50. Moreover, water in the atmosphere becomes attached to the surface of the particle 51, and at this time water 52 from the atmosphere is trapped between the particle 51 and the surface of the wafer 50 (FIG. 4A).

Figure 4B:
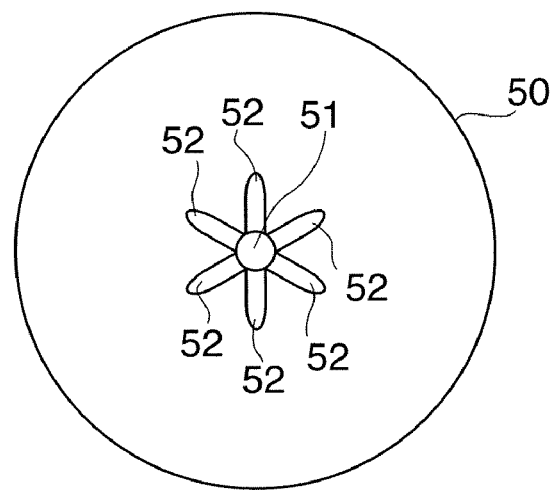

(2) Upon the wafer 50 being transferred into the load lock module, the atmospheric gate valve being closed, and the load lock module being evacuated, a state of adiabatic expansion is produced due to the pressure decreasing suddenly in the load lock module, and hence the water trapped between the particle 51 and the surface of the wafer 50 freezes. At this time, the frozen water 52 grows in a snow crystal shape (FIG. 4B). Here, "snow crystal shape" means a shape characterized by being branched with six-fold symmetry due to hydrogen bonding between water molecules.

Figure 4C:
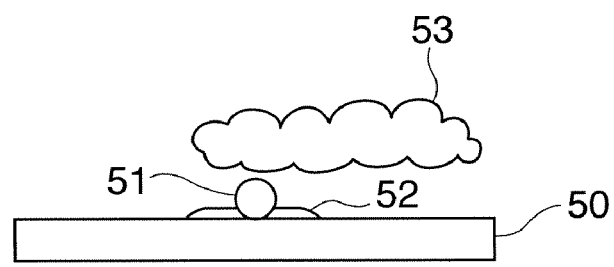

(3) After that, upon the vacuum gate valve being opened, residual gas 53, for example gas containing a halogen such as fluorine, from the processing gas used in the RIE processing on another wafer flows into the load lock module from the processing chamber of the processing module. The fluorine of the residual gas 53 becomes attached to the frozen water 52 (FIG. 4C).

Figure 4D:
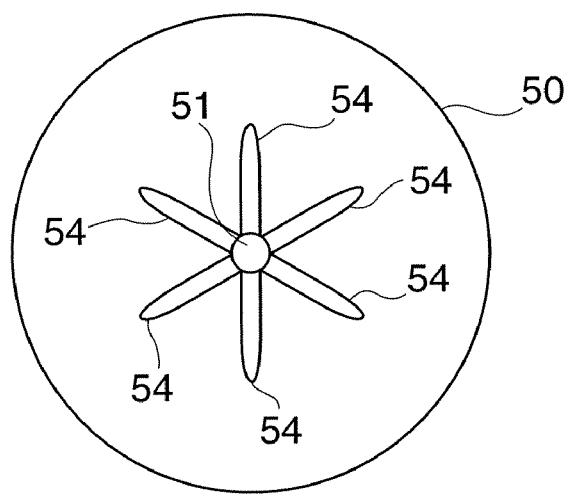

(4) Next, upon nitrogen gas or the like being introduced into the load lock module so as to release the load lock module to atmospheric pressure, the frozen water 52 melts. At this time, the fluorine attached to the water 52 combines with the water to form hydrogen fluoride. The hydrogen fluoride corrodes a substance, for example silicon, exposed at the surface of the wafer, so that corrosion marks are formed on the surface of the wafer. Moreover, due to melting, the water 52 spreads over the surface of the wafer, and hence corroded portions 54, which are the corrosion marks due to the hydrogen fluoride, are also enlarged. The corroded portions 54 thus become larger in size than the particle 51. As a result, the presence of the particle 51 is emphasized by the corroded portions 54 (FIG. 4D).

Through the above, it was found that if a substance that alters, for example corrodes, a substance exposed at the surface of a wafer is trapped between a particle attached to the surface of the wafer and the surface of the wafer, then altered portions, for example corroded portions, can be formed around the particle so as to emphasize the presence of the particle.

The present invention is based on the above finding.

Next, pre-inspection surface processing and substrate surface inspection processing carried out in the substrate processing system according to the present embodiment will be described. Here, the pre-inspection surface processing uses alteration of a substance exposed at the surface of a wafer. The pre-inspection surface processing and the substrate surface inspection processing are carried out by the system controller in accordance with predetermined programs.

FIGS. 5A to 5E are process drawings of the pre-inspection surface processing and the substrate surface inspection processing carried out in the substrate processing system according to the present embodiment.

Figure 5A:
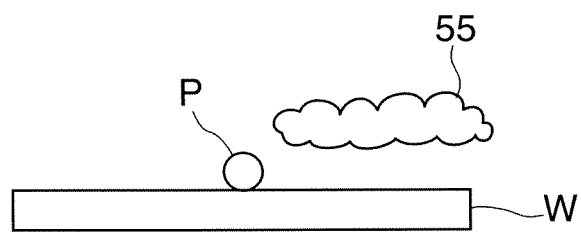
FIGS. 5A to 5E are process drawings of pre-inspection surface processing and substrate surface inspection processing carried out in the substrate processing system according to the above embodiment.

First, a wafer W to the surface of which a particle P of size approximately 30 nm has become attached through the wafer W being transferred through the loader module 13 or transferred into a load lock module 27 which is open to atmospheric pressure is transferred into the housing chamber 34 of the surface processing apparatus 17. Next, a fluorine-containing gas 55 produced through decomposition of a CF type gas is supplied into the housing chamber 34 from the fluid supply unit 36 (FIG. 5A). As a result, the gas 55 is supplied onto the surface of the wafer W so that fluorine is attached to the surface.

Figure 5B:
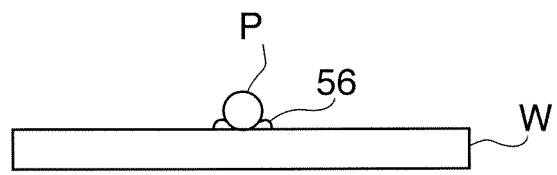

Next, a water-containing gas is supplied into the housing chamber 34. Note that to prevent hydrogen fluoride from being produced in the fluid supply unit 36, it is preferable for the water-containing gas to be supplied in using supply means (not shown) other than the fluid supply unit 36. As a result of the above, the water-containing gas is supplied onto the surface of the wafer W so that water 56 is trapped between the particle P and the surface of the wafer W. Moreover, the water 56 combines with the fluorine attached to the surface of the wafer W, so that hydrogen fluoride is produced (FIG. 5B).

Figure 5C:
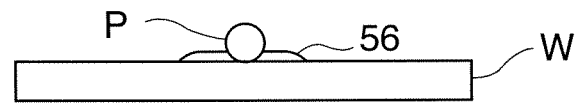

Next, the gate valve 37 is closed, and the pressure in the housing chamber 34 is reduced using the exhaust unit 38. At this time, a state of adiabatic expansion is produced in the housing chamber 34, and hence the water 56 trapped between the particle P and the surface of the wafer W freezes, and grows in a snow crystal shape (FIG. 5C).

Figure 5D:
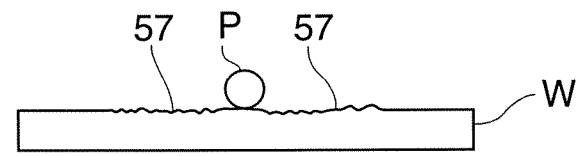

Next, the gate valve 37 is opened so as to make the interior of the housing chamber 34 be at atmospheric pressure, whereupon the frozen water 56 melts and spreads over the surface of the wafer W. The wafer W is then left in the housing chamber 34 for a predetermined time period, for example 1 second to 10 minutes, preferably 1 to 60 seconds. During this time period, the hydrogen fluoride contained in the water 56 sufficiently corrodes silicon exposed at the surface of the wafer W. As a result, corrosion marks (corroded portions) 57 larger than the particle P are formed around the particle P (FIG. 5D). When viewed from above the wafer W, the corroded portions 57 exhibit a snow crystal-shaped pattern. Moreover, the surface becomes rough at the corroded portions 57.

Figure 5E:
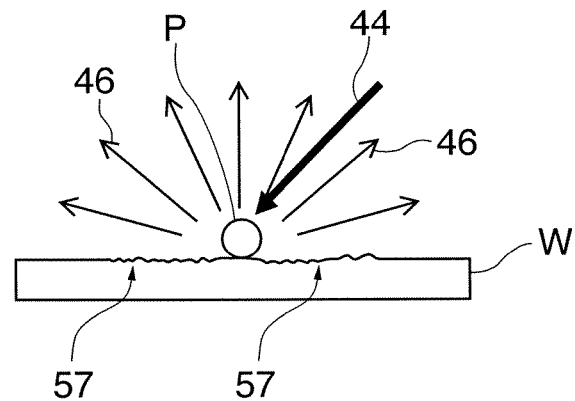

Next, the wafer W is transferred out from the surface processing apparatus 17, and transferred into the housing chamber 42 of the surface inspecting apparatus 18 and mounted on the wafer stage 43. The wafer stage 43 then rotates the wafer W. Moreover, the laser beam irradiating unit 45 irradiates the laser beam 44 onto the surface of the wafer W. Here, because the surface is rough at the corroded portions 57, the laser beam 44 is scattered not only by the particle P but also by the corroded portions 57, so that much scattered light 46 is produced (FIG. 5E). The amount of light received by the light receiver 47 is thus increased, and hence the voltage of the electrical signal obtained through the conversion by the photoelectric converter 48 is also increased. As a result, the presence of the corroded portions 57, and hence the presence of the particle P, can easily be detected.

Note that FIGS. 5A to 5D correspond to the pre-inspection surface processing, and FIG. 5E corresponds to the substrate surface inspection processing.

According to the processing of FIGS. 5A to 5E described above, the fluorine-containing gas 55 and the water-containing gas are supplied onto the surface of the wafer W, and then the surface of the wafer W onto which the gas 55 and the water-containing gas have been supplied is inspected. In the case that a particle P is attached to the surface of the wafer W, hydrogen fluoride-containing water 56 is trapped between the particle P and the wafer W, and the hydrogen fluoride contained in the water 56 corrodes silicon exposed at the surface of the wafer W. As a result, corroded portions 57 are formed around the particle P, the corroded portions 57 being larger in size than the particle P. Moreover, the laser beam 44 is scattered by not only the particle P but also the corroded portions 57, and hence by detecting the corroded portions 57, the particle P can be detected easily. There is thus no need to examine the surface of the wafer W with an SEM, and hence a minute particle P attached to the surface of the wafer W can be detected using a method suitable for mass production of wafers W.

In the processing of FIGS. 5A to 5E described above, the pressure in the housing chamber 34 in which the wafer W is housed is reduced, so that the hydrogen fluoride-containing water 56 trapped between the particle P and the surface of the wafer W freezes through adiabatic expansion, and thus stays around the particle P reliably. As a result, the corroded portions 57 can be formed around the particle P reliably.

In the processing of FIGS. 5A to 5E described above, after the gas 55 and the water-containing gas have been supplied onto the surface of the wafer W, the wafer W is left for a predetermined time period in the housing chamber 34. While the wafer W is being left, the hydrogen fluoride contained in the water 56 sufficiently corrodes the silicon exposed at the surface of the wafer W. As a result, the corroded portions 57 are formed around the particle P reliably, and hence the particle P can be detected yet more easily.

Moreover, in the surface inspecting apparatus 18 of the substrate processing system 10 described above, the wafer W is rotated, the surface of the wafer W is irradiated with the laser beam 44, and some of scattered light scattered from the surface is converted into an electrical signal. As a result, the particle P having the corroded portions 57 formed therearound can be detected efficiently. Moreover, the surface inspecting apparatus 18 has the same structure as a conventional substrate surface inspecting apparatus that uses a scattered laser light method, and hence the manufacturing cost of the substrate processing system 10 can be reduced.

In the processing of FIGS. 5A to 5E described above, the fluid supplied into the housing chamber 34 is comprised of a fluorine-containing gas 55 and a water-containing gas; however, the fluid supplied into the housing chamber 34 is not limited thereto, but rather may be any fluid containing an acid, an alkali, a substance that combines with another substance to form an acid, or a substance that combines with another substance to form an alkali. Examples of such a fluid include a CF type gas, or a solution, gas, or supercritical fluid containing ammonium fluoride, hot phosphoric acid, nitric acid, glacial acetic acid, ammonium hydroxide, hydrogen peroxide, ozone, chlorine, hydrogen sulfide, hydrogen chloride, hydrogen bromide, potassium hydroxide, xenon fluoride, sulfur hexafluoride, or tetramethylammonium hydroxide (TMAH). These substances are able to alter, for example corrode or erode, a substance exposed at the surface of a wafer W, so as to form corrosion or erosion marks larger than a particle P around the particle P.

The substance contained in the fluid supplied into the housing chamber 34 is not limited to being one that alters (corrodes) the substance exposed at the surface of the wafer W, but rather may instead be a substance that is trapped between a particle P and the surface of the wafer W and forms a residue around the particle P upon evaporating upon releasing to atmospheric pressure, examples including methanol, ethanol, glycol ethers (IPA) (IPA は, isopropyl alchol ではないでしょうか？ご確認ください), acetone, toluene, and water containing a non-volatile impurity. When such a substance melts out around a particle P from between the particle P and the surface of the wafer W and further evaporates upon releasing to atmospheric pressure, a residue larger in size than the particle P is formed around the particle P. The residue scatters the laser beam 44, and hence the amount of scattered light 46 can be increased. By detecting the residue, the particle P can thus be detected easily.

In the case that a substance not readily eroded or corroded is exposed at the surface of the wafer W, it is preferable to form on this substance a film or the like of a substance that is readily eroded or corroded. As a result, eroded portions or corroded portions can easily be formed around a particle P.

In the processing of FIGS. 5A to 5E described above, the pressure in the housing chamber 34 in which the wafer W is housed is reduced; however, the hydrogen fluoride contained in the water trapped between a particle P and the surface of the wafer W is able to corrode the exposed substance around the particle P before the water freezes, and hence the water need not necessarily be frozen to form the corroded portions. That is, the pressure in the housing chamber 34 need not necessarily be reduced. In this case, the water trapped between the particle P and the surface of the wafer W will somewhat run out therefrom due to surface tension, so that the corroded portions become larger in size than the particle P. As a result, the particle P can easily be detected even if the pressure in the housing chamber 34 is not reduced.

Moreover, in the processing of FIGS. 5A to 5E described above, first the gas 55 is supplied onto the surface of the wafer W; however, it is instead possible to supply in the water-containing gas without supplying in the gas 55, reduce the pressure in the housing chamber 34 so as to make the water 56 grow in a snow crystal shape around a particle P, and then supply in from the fluid supply unit 36 a gas that reacts with water to produce a solid, for example a gas containing a cyanoacrylate (cyanoacrylic acid ester) (reactive substance), whereby a solid can be formed in a snow crystal shape around the particle P on the surface of the wafer W. Specifically, the following chemical reaction is used.

[FORMULA 1]

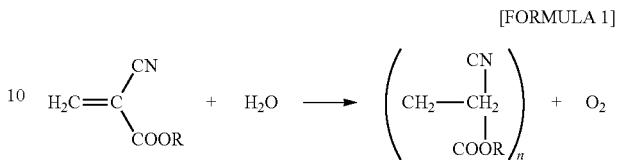

The cyanoacrylate reacts with the water, polymerizing and hardening to become a polycyanoacrylate. The solid polycyanoacrylate thus formed will not evaporate upon releasing to atmospheric pressure. That is, the snow crystal-shaped solid remains around the particle P. The solid scatters the laser beam 44, and hence the amount of scattered light 46 can be increased. By detecting the solid, the particle P can thus be detected easily.

The gas that reacts with the water to produce the solid is a vaporized cyanoacrylate type solvent. The cyanoacrylate type solvent is a mixture having an alkyl cyanoacrylate, specifically methyl cyanoacrylate, ethyl cyanoacrylate, octyl cyanoacrylate, butyl cyanoacrylate, methoxyethyl cyanoacrylate or the like, as a main component thereof, and containing a ketone as a diluent.

Next, a substrate processing system according to a second embodiment of the present invention will be described.

The present embodiment is basically the same as the first embodiment described above in terms of construction and operation, only the construction of the surface inspecting apparatus differing to in the first embodiment. Features of the construction that are the same as in the first embodiment will thus not be described, only features of the construction and operation that are different to in the first embodiment being described below.

Figure 6A:
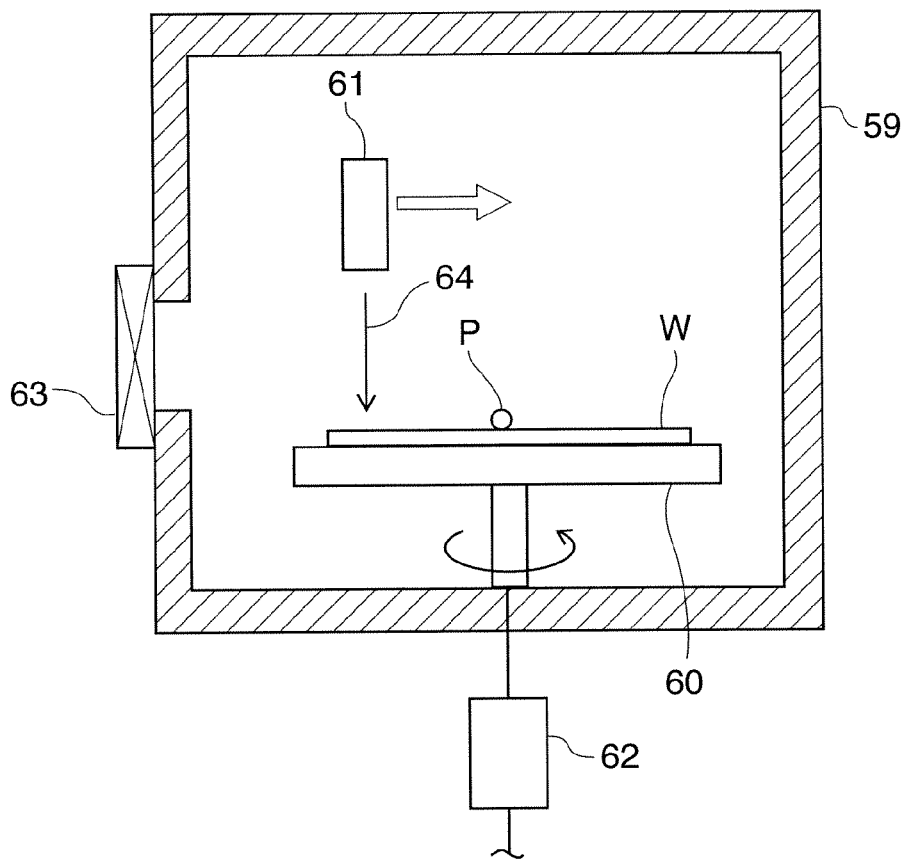
FIGS. 6A and 6B are diagrams schematically showing the construction of a surface inspecting apparatus of a substrate processing system according to a second embodiment of the present invention, FIG. 6A being a sectional view of the surface inspecting apparatus, and FIG. 6B being a graph showing a current due to an EB upon a surface of a wafer being irradiated with the EB in the surface inspecting apparatus.
Figure 6B:
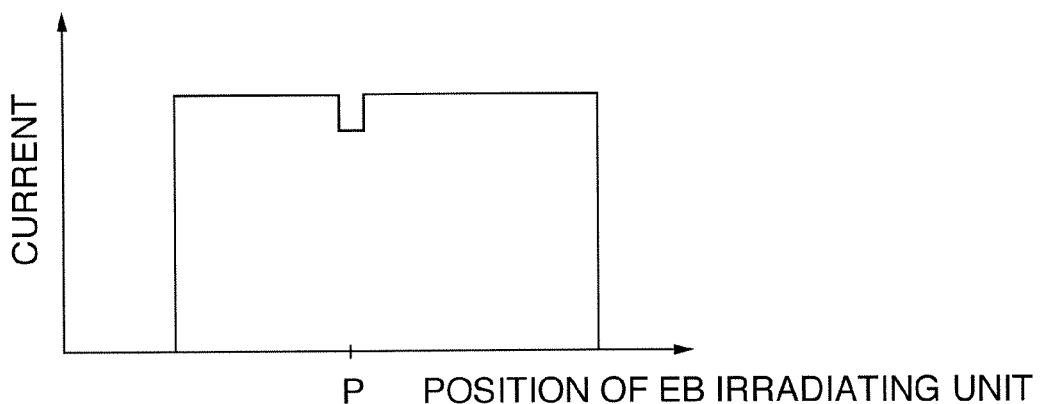

FIG. 6 are diagrams schematically showing the construction of the surface inspecting apparatus of the substrate processing system according to the present embodiment, FIG. 6A being a sectional view of the surface inspecting apparatus, and FIG. 6B being a graph showing a current due to an EB upon a surface of a wafer being irradiated with the EB in the surface inspecting apparatus.

As shown in FIG. 6A, the surface inspecting apparatus 58 is comprised of a box-shaped housing chamber 59, a wafer stage 60 (stage) that is disposed in a lower portion of the housing chamber 59 and on which a wafer W is mounted and rotated, an EB irradiating unit 61 that irradiates an EB 64 onto a surface of the rotating wafer W, a current measuring unit 62 that is connected to the wafer stage 60 and measures a current produced due to the EB 64 irradiated onto the wafer W mounted on the wafer stage 60, and an openable/closable gate valve 63 that is disposed in a side of the housing chamber 59. The EB irradiating unit 61 can be moved while being kept facing the wafer W mounted on the wafer stage 60, and hence the whole surface of the wafer W can be scanned by the EB 64. The current measuring unit 62 is connected to the system controller.

The surface inspecting apparatus 58 is connected to the loader module 13 via the gate valve 63, the interior of the housing chamber 59 being communicated with the interior of the loader module 13 when the gate valve 63 is open.

In the surface inspecting apparatus 58, in the case that a particle P is attached to the surface of the wafer W mounted on the wafer stage 60, upon the particle P being irradiated by the EB 64, the particle P captures electrons in the EB 64, and hence the value of the current flowing through the wafer W and the wafer stage 60 produced due to the EB 64 (hereinafter referred to merely as "the current") is reduced (see FIG. 6B). The value of the current is measured by the current measuring unit 62 and sent to the system controller. The amount of electrons captured changes in accordance with the size of the particle P, and hence the system controller detects the size of the particle P based on the value of the current upon the particle P being irradiated by the EB 64.

The pre-inspection surface processing carried out in the substrate processing system according to the present embodiment is the same as the pre-inspection surface processing carried out in the substrate processing system according to the first embodiment (FIGS. 5A to 5D), and hence description will not be given here, only the substrate surface inspection processing carried out in the substrate processing system according to the present embodiment being described below.

In the substrate surface inspection processing carried out in the substrate processing system according to the present embodiment, a wafer W is transferred out from the surface processing apparatus 17, and transferred into the housing chamber 59 of the surface inspecting apparatus 58 and mounted on the wafer stage 60. The wafer stage 60 then rotates the wafer W. Moreover, the EB irradiating unit 61 scans the whole surface of the wafer W with the EB 64. Here, corroded portions 57 have been altered so as to have reduced conductivity, and hence electrons in the EB 64 are captured by not only a particle P but also the corroded portions 57 on the wafer W, whereby the value of the current is reduced when the corroded portions 57 are irradiated by the EB 64. During the scanning by the EB 64, the proportion for which the value of the current is reduced is thus increased. As a result, the presence of the corroded portions 57 and the particle P can easily be detected by measuring the current.

According to the substrate processing system of the present embodiment, in the surface inspecting apparatus 58, the surface of the wafer W is scanned by the EB 64, and the current flowing through the wafer W and the wafer stage 60 produced due to the EB 64 is measured. A particle P attached to the surface of the wafer W and corroded portions 57 capture electrons, and hence when any of the particle P and the corroded portions 57 is irradiated by the EB 64, the value of the current decreases. That is, during the scanning by the EB 64, the proportion for which the value of the current decreases is increased. A minute particle P having corroded portions 57 formed therearound can thus be detected accurately. Moreover, because the minute particle P can be detected merely by measuring the current, the particle P can be detected more efficiently.

Next, a substrate processing system according to a third embodiment of the present invention will be described.

The present embodiment is basically the same as the first embodiment described above in terms of construction and operation, only the construction of the surface inspecting apparatus differing to in the first embodiment. Features of the construction that are the same as in the first embodiment will thus not be described, only features of the construction and operation that are different to in the first embodiment being described below.

Figure 7A:
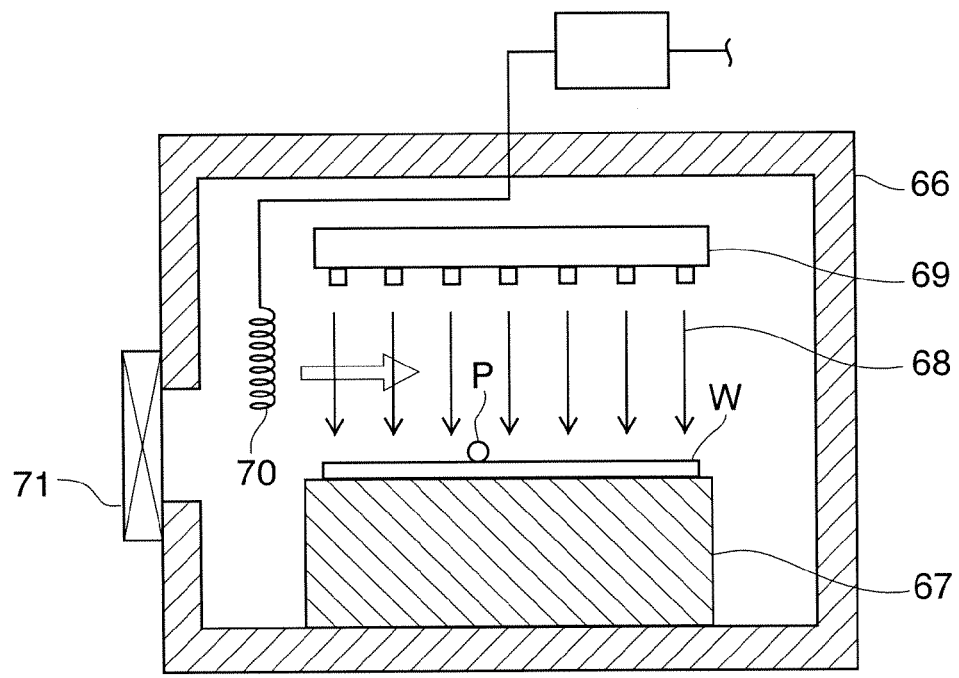
FIGS. 7A and 7B are diagrams schematically showing the construction of a surface inspecting apparatus of a substrate processing system according to a third embodiment of the present invention, FIG. 7A being a sectional view of the surface inspecting apparatus, and FIG. 7B being a graph showing a charge distribution over a surface of a wafer upon the whole surface of the wafer being irradiated with EBs in the surface inspecting apparatus.
Figure 7B:
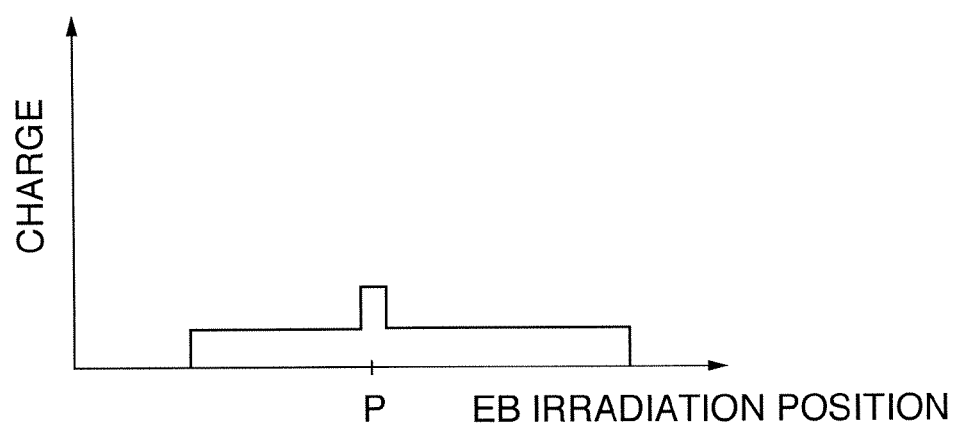

FIGS. 7A and 7B are diagrams schematically showing the construction of the surface inspecting apparatus of the substrate processing system according to the present embodiment, FIG. 7A being a sectional view of the surface inspecting apparatus, and FIG. 7B being a graph showing a charge distribution over a surface of a wafer upon the whole surface of the wafer being irradiated with EBs in the surface inspecting apparatus.

As shown in FIG. 7A, the surface inspecting apparatus 65 is comprised of a box-shaped housing chamber 66, a wafer stage 67 that is disposed in a lower portion of the housing chamber 66 and on which a wafer W is mounted, an EB irradiating unit 69 that irradiates EBs 68 over the whole of a surface of the mounted wafer W, a charge measuring unit 70 that measures a charge on the wafer W mounted on the wafer stage 67, and an openable/closable gate valve 71 that is disposed in a side of the housing chamber 66. The charge measuring unit 70 has a coil or the like, and can be moved while being kept facing the wafer W mounted on the wafer stage 67; an induced current is produced in the charge measuring unit 70 in accordance with the charge on the surface of the wafer W. By measuring the induced current while the charge measuring unit 70 is being moved, the charge distribution over the surface of the wafer W can thus be measured. The charge measuring unit 70 is connected to the system controller.

The surface inspecting apparatus 65 is connected to the loader module 13 via the gate valve 71, the interior of the housing chamber 66 being communicated with the interior of the loader module 13 when the gate valve 71 is open.

In the surface inspecting apparatus 65, in the case that a particle P is attached to the surface of the wafer W mounted on the wafer stage 67, upon the whole surface of the wafer W being irradiated by the EBs 68, the particle P captures electrons in EBs 68, and hence the charge increases at the location of the particle P on the surface of the wafer W (see FIG. 7B). The magnitude of the charge is measured by the charge measuring unit 70 and sent to the system controller. The amount of electrons captured changes in accordance with the size of the particle P, and hence the system controller detects the size of the particle P based on the magnitude of the charge.

The pre-inspection surface processing carried out in the substrate processing system according to the present embodiment is the same as the pre-inspection surface processing carried out in the substrate processing system according to the first embodiment (FIGS. 5A to 5D), and hence description will not be given here, only the substrate surface inspection processing carried out in the substrate processing system according to the present embodiment being described below.

In the substrate surface inspection processing carried out in the substrate processing system according to the present embodiment, a wafer W is transferred out from the surface processing apparatus 17, and transferred into the housing chamber 66 of the surface inspecting apparatus 65 and mounted on the wafer stage 67. The EB irradiating unit 69 then irradiates the whole surface of the wafer W with the EBs 68. Here, corroded portions 57 have been altered so as to have reduced conductivity, and hence electrons in the EBs 68 are captured by not only a particle P but also the corroded portions 57 on the wafer W, whereby the charge increases at the locations of the corroded portions 57. During the measurement of the charge distribution over the whole surface of the wafer W by the charge measuring unit 70, the proportion of places where the charge increases thus increases. As a result, the presence of the corroded portions 57 and the particle P can easily be detected by measuring the charge distribution.

According to the substrate processing system of the present embodiment, the EBs 68 are irradiated over the whole surface of the wafer W, and the charge distribution over the whole surface is measured. A particle P attached to the surface of the wafer W and corroded portions 57 capture electrons, and hence the charge increases at the location of any of the particle P and the corroded portions 57. That is, during the measurement of the charge distribution over the whole surface of the wafer W by the charge measuring unit 70, there is an increase in the proportion of places where the charge increases. By measuring the charge distribution over the whole surface of the wafer W, a minute particle P having corroded portions 57 formed therearound can thus be detected accurately. Moreover, because the minute particle P can be detected merely by measuring the charge distribution, the particle P can be detected more efficiently.

Note that in the substrate processing system according to the present embodiment, the EBs 68 are irradiated over the surface of the wafer W. However, the region irradiated by the EBs 68 is not limited to being the whole surface, but rather may instead by a desired region (a partial region). In this case, the charge measuring unit 70 preferably measures only the charge distribution over the desired region.

Next, a substrate processing system according to a fourth embodiment of the present invention will be described.

The present embodiment is basically the same as the first embodiment described above in terms of construction and operation, only the construction of the surface processing apparatus differing to in the first embodiment. Features of the construction that are the same as in the first embodiment will thus not be described, only features of the construction and operation that are different to in the first embodiment being described below.

The surface processing apparatus (not shown) of the substrate processing system according to the present embodiment is comprised of a housing chamber housing a wafer, and an etching apparatus that etches a substance exposed at a surface of the wafer housed in the housing chamber. Examples of the etching apparatus are an etching apparatus using plasma such as a parallel plate type plasma etching apparatus, an electron cyclotron resonance (ECR) plasma etching apparatus, an inductively coupled plasma (ICP) plasma etching apparatus, an RLSA (radial line slot antenna) microwave plasma etching apparatus or a remote plasma etching apparatus, or a wet etching apparatus that etches with a fluid (liquid, gas, or supercritical fluid) containing a substance that corrodes or erodes the substance exposed at the surface of the wafer W. Note that the construction of each of these examples of the etching apparatus is publicly known, and hence description will not be given here.

Next, pre-inspection surface processing and substrate surface inspection processing carried out in the substrate processing system according to the present embodiment will be described.

FIGS. 8A to 8D are process drawings of the pre-inspection surface processing and the substrate surface inspection processing carried out in the substrate processing system according to the present embodiment.

Figure 8A:
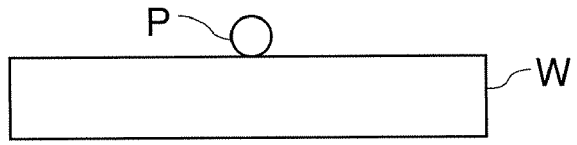
FIGS. 8A to 8D are process drawings of pre-inspection surface processing and substrate surface inspection processing carried out in a substrate processing system according to a fourth embodiment of the present invention.
Figure 8B:
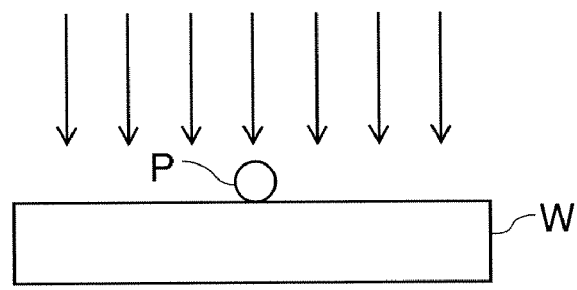
Figure 8C:
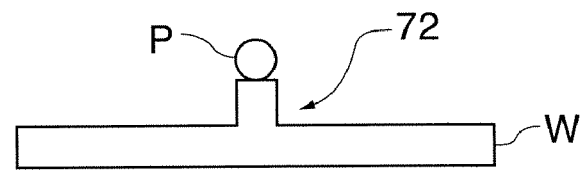

First, a wafer W to the surface of which a particle P of size approximately 30 nm has become attached through the wafer W being transferred through he loader module or transferred into a load lock module which is open to atmospheric pressure is transferred into the housing chamber of the surface processing apparatus (FIG. 8A). Next, the surface of the wafer W to which the particle P is attached is etched by the etching apparatus (FIG. 8B). At this time, the particle P acts as a micro-mask, and hence the substance present below the particle P is not etched. As a result, a projection 72 projecting out from the surface of the wafer W and having the particle P on top thereof is formed (FIG. 8C).

Next, the wafer W is transferred out from the surface processing apparatus, and transferred into the housing chamber 42 of the surface inspecting apparatus 18 and mounted on the wafer stage 43. The wafer stage 43 then rotates the wafer W.

Figure 8D:
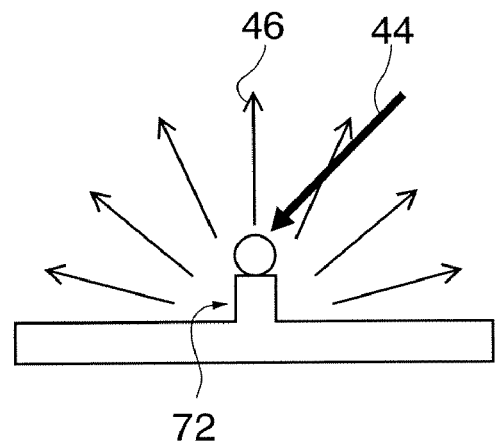

Moreover, the laser beam irradiating unit 45 irradiates the laser beam 44 onto the surface of the wafer W. Here, because the projection 72 projects out from the surface of the wafer W, the projection 72 scatters the laser beam 44 well (FIG. 8D). The amount of scattered light 46 received by the light receiver 47 is thus increased, and hence the voltage of the electrical signal obtained through the conversion by the photoelectric converter 48 is also increased. As a result, the presence of the particle P can easily be detected.

According to the substrate processing system of the present embodiment, the surface of the wafer W is etched, and then the etched surface of the wafer W is inspected using the scattered laser light method. In the case that a particle P is attached to the surface of the wafer W, upon the surface of the wafer W being etched, the particle P acts as a micro-mask so that the substance below the particle P is not etched, whereby a projection 72 having the particle P on top thereof is formed. The projection 72 scatters the laser beam well, and hence can easily be detected. There is thus no need to examine the surface of the wafer W with an SEM, and hence a minute particle P attached to the surface of the wafer W can be detected using a method suitable for mass production of wafers W.

Examples of the fluid used in the wet etching apparatus described above include a CF type gas, or a solution, gas, or supercritical fluid containing hydrogen fluoride, ammonium fluoride, hot phosphoric acid, nitric acid, hydrochloric acid, sulfuric acid, glacial acetic acid, ammonium hydroxide, hydrogen peroxide, ozone, chlorine, hydrogen sulfide, hydrogen chloride, hydrogen bromide, potassium hydroxide, xenon fluoride, sulfur hexafluoride, or tetramethylammonium hydroxide.

Next, a substrate processing system according to a fifth embodiment of the present invention will be described.

The present embodiment is basically the same as the first embodiment described above in terms of construction and operation, only the construction of the surface processing apparatus differing to in the first embodiment. Features of the construction that are the same as in the first embodiment will thus not be described, only features of the construction and operation that are different to in the first embodiment being described below.

The surface processing apparatus (not shown) of the substrate processing system according to the present embodiment is comprised of a housing chamber housing a wafer, a stepper (exposing unit) that exposes to light a positive resist coating film on a surface of the wafer housed in the housing chamber, and a developer (developing unit) that develops the exposed positive resist coating film with a strongly alkaline developing solution. Here, the positive resist coating film on the surface of the wafer is formed before the wafer is transferred through the loader module 13 or transferred into a load lock module 27 which is open to atmospheric pressure. Each of the stepper and the developer has a publicly known construction, and hence description will not be given here.

Next, pre-inspection surface processing and substrate surface inspection processing carried out in the substrate processing system according to the present embodiment will be described.

FIGS. 9A to 9E are process drawings of the pre-inspection surface processing and the substrate surface inspection processing carried out in the substrate processing system according to the present embodiment.

Figure 9A:
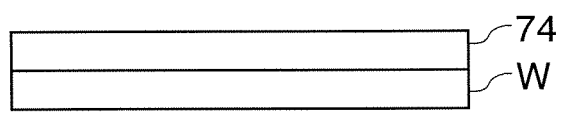
FIGS. 9A to 9E are process drawings of pre-inspection surface processing and substrate surface inspection processing carried out in a substrate processing system according to a fifth embodiment of the present invention.
Figure 9B:
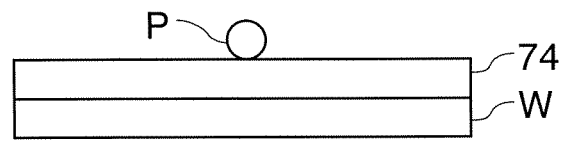

First, a positive resist coating film 74 is formed by spin coating or the like on a surface of a wafer W (FIG. 9A), and the wafer W is transferred through the loader module 13 or transferred into a load lock module 27 which is open to atmospheric pressure. At this time, a particle P of size approximately 30 nm may become attached to the surface of the wafer W (FIG. 9B).

Figure 9C:
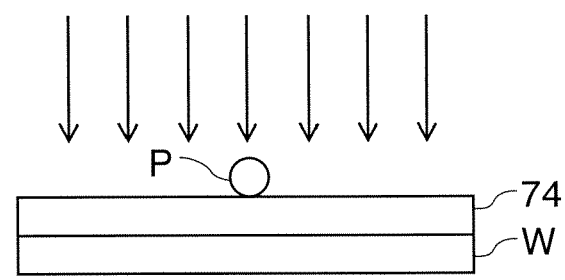

Next, the wafer W is transferred into the housing chamber of the surface processing apparatus, and the positive resist coating film 74 on the surface of the wafer W is exposed to light by the stepper (FIG. 9C). At this time, the particle P acts as a micro-mask, and hence the positive resist is not exposed below the particle P, and thus the structure of the positive resist here does not change into a chemical structure that will dissolve in an alkaline solution (i.e. is not altered through photochemical reaction). On the other hand, in places other than below the particle P, the positive resist is exposed, and hence the structure thereof does change into a chemical structure that will dissolve in an alkaline solution.

Figure 9D:
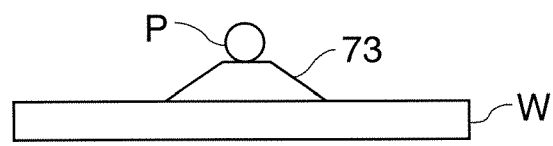

Next, a strongly alkaline developing solution is dripped onto the exposed positive resist coating film 74, whereby the positive resist dissolves and is thus removed; however, the positive resist does not dissolve below the particle P. As a result, a hill-like projection 73 having the particle P on top thereof is formed on the surface of the wafer W (FIG. 9D).

Figure 9E:
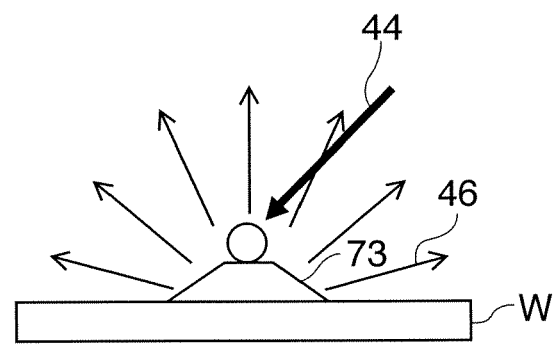

Next, the wafer W is transferred out from the surface processing apparatus, and transferred into the housing chamber 42 of the surface inspecting apparatus 18 and mounted on the wafer stage 43. The wafer stage 43 then rotates the wafer W. Moreover, the laser beam irradiating unit 45 irradiates the laser beam 44 onto the surface of the wafer W. Here, because the projection 73 projects out from the surface of the wafer W, the projection 73 scatters the laser beam 44 well (FIG. 9E). The amount of scattered light 46 received by the light receiver 47 is thus increased, and hence the voltage of the electrical signal obtained through the conversion by the photoelectric converter 48 is also increased. As a result, the presence of the particle P can easily be detected.

According to the substrate processing system of the present embodiment, the positive resist coating film 74 formed on the surface of the wafer W is exposed to light, the exposed positive resist is developed, and then the surface of the wafer W on which the positive resist has been developed is inspected. In the case that a particle P is attached to the surface of the wafer W on which the positive resist coating film 74 has been formed, upon the surface being exposed, the particle P acts as a mask so that the positive resist is not exposed below the particle P, and thus does not change into a chemical structure that will dissolve in an alkaline solution. That is, below the particle P, the positive resist is not dissolved by the strongly alkaline developing solution, and as a result a hill-like projection 73 having the particle P on top thereof is formed on the surface of the wafer W. The projection 73 scatters the laser beam well, and hence can easily be detected. There is thus no need to examine the surface of the wafer W with an SEM, and hence a minute particle P attached to the surface of the wafer W can be detected using a method suitable for mass production of wafers W.

Next, a substrate processing system according to a sixth embodiment of the present invention will be described.

The present embodiment is basically the same as the first embodiment described above in terms of construction and operation, only the construction of the surface processing apparatus differing to in the first embodiment. Features of the construction that are the same as in the first embodiment will thus not be described, only features of the construction and operation that are different to in the first embodiment being described below.

Figure 10:
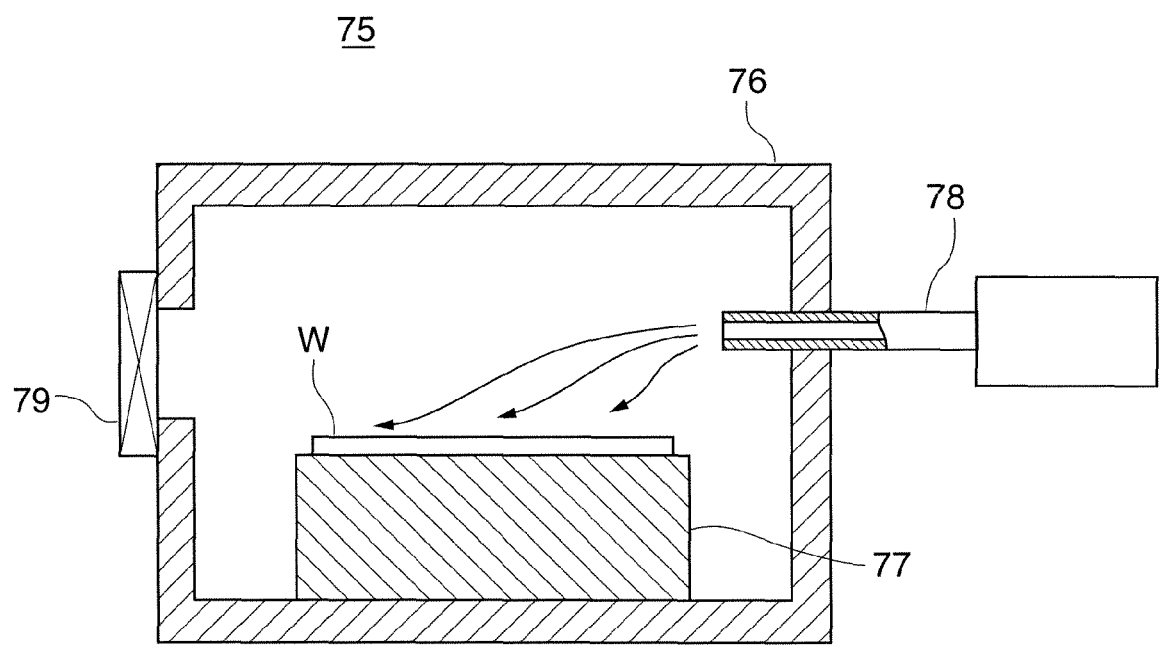
FIG. 10 is a sectional view schematically showing the construction of a surface processing apparatus of a substrate processing system according to a sixth embodiment of the present invention.

FIG. 10 is a sectional view schematically showing the construction of the surface processing apparatus of the substrate processing system according to the present embodiment. A direction that is upward in FIG. 10 will be referred to as "above" or "upper", and a direction that is downward in FIG. 10 as "below" or "lower".

As shown in FIG. 10, the surface processing apparatus 75 is comprised of a box-shaped housing chamber 76, a rapid cooling stage 77 that is disposed in a lower portion of the housing chamber 76, has a wafer W mounted thereon, and rapidly cools the mounted wafer W, a fluid supply unit 78 that is disposed in an upper portion of the housing chamber 76 and supplies a predetermined fluid, for example a gas as described above that reacts with water to produce a solid, into the housing chamber 76, an openable/closable gate valve 79 that is disposed in a side of the housing chamber 76, and an exhaust unit (not shown) that exhausts the fluid out from the housing chamber 76. The surface processing apparatus 75 is connected to the loader module 13 via the gate valve 79, the interior of the housing chamber 76 being communicated with the interior of the loader module 13 when the gate valve 79 is open.

The rapid cooling stage 77 has therein a coolant chamber (not shown) as a rapid cooling mechanism. A coolant, for example cooling water or a Galden fluid, at a predetermined temperature is circulated through the coolant chamber, the wafer W which is mounted on an upper surface of the rapid cooling stage 77 being rapidly cooled through the temperature of the coolant. Alternatively, the rapid cooling stage 77 may have a rapid cooling mechanism having a cooling fan, a heat sink, and a cooling plate disposed on an upper surface of the heat sink.

Next, pre-inspection surface processing and substrate surface inspection processing carried out in the substrate processing system according to the present embodiment will be described.

FIGS. 11A to 11E are process drawings of the pre-inspection surface processing and the substrate surface inspection processing carried out in the substrate processing system according to the present embodiment.

Figure 11A:
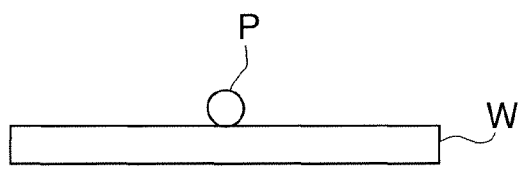
FIGS. 11A to 11E are process drawings of pre-inspection surface processing and substrate surface inspection processing carried out in the substrate processing system according to the sixth embodiment of the present invention.
Figure 11D:
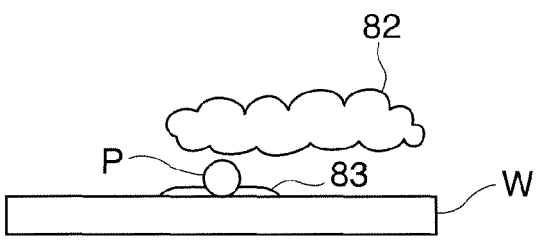
Figure 11B:
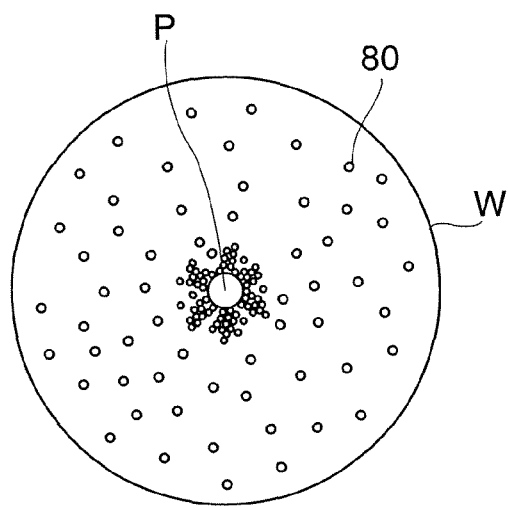

As shown in FIGS. 11A to 11E, first, a wafer W to the surface of which a particle P of size approximately 30 nm has become attached through the wafer W being transferred through the loader module 13 or transferred into a load lock module 27 which is open to atmospheric pressure (FIG. 11A) is transferred into the housing chamber 76 of the surface processing apparatus 75, and mounted on the rapid cooling stage 77. Next, the rapid cooling stage 77 rapidly cools the wafer W mounted on the upper surface thereof to a temperature of not more than 0° C., preferably not more than −5° C. At this time, water in the atmosphere is put into a supercooled state on the surface of the wafer W, and hence supercooled water 80 is produced on the surface of the wafer W (FIG. 11B). Moreover, the supercooled water 80 collects around the particle P as shown in FIG. 11B, and the collected supercooled water 80 is released from the supercooled state and thus freezes. At this time, the frozen water 81 grows in a snow crystal shape as described earlier (FIG. 11C).

Next, a gas 82 that reacts with water to produce a solid as described earlier is supplied into the housing chamber 76 from the fluid supply unit 78. As a result, the gas 82 is supplied onto the surface of the wafer W, so that the gas 82 reacts with the frozen water 81 to produce solid 83. As a result, solid 83 larger in size than the particle P is formed around the particle P (FIG. 11D). When viewed from above the wafer W, the solid 83 exhibits a snow crystal-shaped pattern.

Figure 11E:
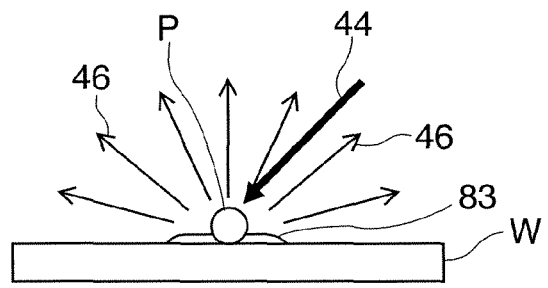
Figure 11C:
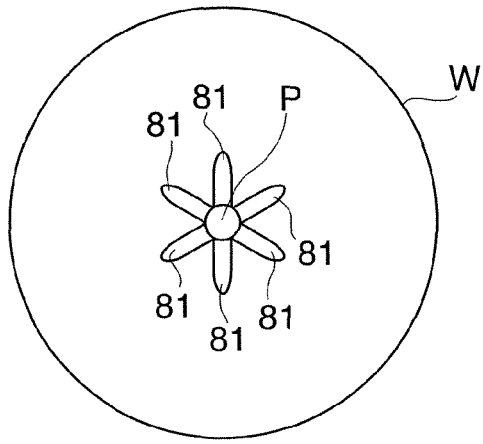

Next, the wafer W is transferred out from the surface processing apparatus 75, and transferred into the housing chamber 42 of the surface inspecting apparatus 18 and mounted on the wafer stage 43. The wafer stage 43 then rotates the wafer W. Moreover, the laser beam irradiating unit 45 irradiates the laser beam 44 onto the surface of the wafer W. Here, because the snow crystal-shaped solid 83 is formed on the surface of the wafer W, the laser beam 44 is scattered not only by the particle P but also by the solid 83, so that much scattered light 46 is produced (FIG. 11E). The amount of scattered light 46 received by the light receiver 47 is thus increased, and hence the voltage of the electrical signal obtained through the conversion by the photoelectric converter 48 is also increased. As a result, the presence of the solid 83, and hence the presence of the particle P, can easily be detected.

Furthermore, in the case that a minute scratch is formed on the surface of the wafer W due to washing processing or the like carried out on the wafer W, again, as in the above case that a particle P is attached to the surface of the wafer W, the supercooled water freezes in a snow crystal shape around the scratch. At this time, upon the gas that reacts with water to produce a solid being supplied in, solid is formed around the scratch. The presence of a minute scratch formed on the surface of the wafer W can thus similarly be easily detected.

According to the substrate processing system of the present embodiment, the wafer W is cooled rapidly, the gas 82 that reacts with water to produce a solid is supplied onto the surface of the rapidly cooled wafer W, and then the surface of the wafer W onto which the gas 82 has been supplied is inspected. In the case that a particle P is attached to the surface of the wafer W, supercooled water 80 produced through the rapid cooling of the wafer W collects and freezes around the particle P, and the frozen water 81 reacts with the gas 82 supplied onto the surface of the wafer W. As a result, solid 83 is formed around the particle P, the solid 83 being larger in size than the particle P. Moreover, the laser beam 44 is scattered by not only the particle P but also the solid 83, and hence by detecting the solid 83, the particle P can be detected easily. There is thus no need to examine the surface of the wafer W with an SEM, and hence a minute particle P attached to the surface of the wafer W can be detected using a method suitable for mass production of wafers W. Moreover, in the case that a minute scratch is formed on the surface of the wafer W, again, solid is formed around the scratch, whereby the minute scratch formed on the surface of the wafer W can be similarly detected.

In each of the embodiments described above, the substrate processing system has a surface processing apparatus and a surface inspecting apparatus. However, the surface processing apparatus may be disposed separate to the substrate processing system, or the surface inspecting apparatus may be disposed separate to the substrate processing system. Furthermore, such a separate surface inspecting apparatus may have therein the component elements of any of the surface processing apparatuses described above.

Note that in the pre-inspection surface processing and substrate surface inspection processing in the embodiments described above, the size of a particle P is detected based on the magnitude of the scattered light 46 scattered from the surface of the wafer W, the value of a current flowing through the wafer W and a wafer stage 60 produced due to an EB 64, or the magnitude of a charge due to EBs 68 irradiated onto the surface of the wafer W. However, the method of detecting the size of the particle P is not limited thereto. For example, it is surmised that the extent of growth of corroded portions 57 is related to the time period for which the fluoride-containing gas 55 is supplied into the housing chamber 34, and hence the size of a particle P may be inferred based on the time period for which the gas 55 is supplied. Specifically, in the case that it has been found, for example, that with a particle P of size approximately 30 nm, if the gas 55 is supplied in for 3 seconds then the growth of the corroded portions 57 is insufficient and hence the particle P cannot be detected, whereas if the gas 55 is supplied in for 5 seconds then the growth of the corroded portions 57 is sufficient and hence the particle P can be detected, then it could be inferred that the size of a particle P was not more than 30 nm if the particle P could not be detected upon supplying in the gas 55 for 5 seconds.

Moreover, it is conjectured that the amount of fluid trapped between a particle P and the surface of the wafer W changes, and hence the size of the corroded portions 57 also differs, in accordance with the composition of the particle P, and hence the composition of a particle P can be inferred by detecting the size of the corroded portions 57.

Note that the substrates whose surface is inspected using the substrate processing system according to any of the embodiments described above are not limited to being wafers for semiconductor devices, but rather may instead be any of various substrates used in LCDs, FPDs (flat panel displays) or the like, photomasks, CD substrates, printed substrates, or the like.

Moreover, it is to be understood that the object of the present invention can also be attained by supplying to a system or apparatus a storage medium in which a program code of software that realizes the functions of an embodiment described above is stored, and then causing a computer (or CPU, MPU, or the like) of the system or apparatus to read out and execute the program code stored in the storage medium.

In this case, the program code itself read out from the storage medium realizes the functions of the embodiment, and hence the program code and the storage medium in which the program code is stored constitute the present invention.

The storage medium for supplying the program code may be, for example, a floppy (registered trademark) disk, a hard disk, a magnetic-optical disk, an optical disk such as a CD-ROM, a CD-R, a CD-RW, a DVD-ROM, a DVD-RAM, a DVD-RW or a DVD+RW, a magnetic tape, a non-volatile memory card, or a ROM. Alternatively, the program code may be downloaded via a network.

Moreover, it is to be understood that the functions of an embodiment described above may be accomplished not only by executing a program code read out by a computer, but also by causing an OS (operating system) or the like which operates on the computer to perform a part or all of the actual operations based on instructions of the program code.

Furthermore, it is to be understood that the functions of an embodiment described above may be accomplished by writing a program code read out from the storage medium into a memory provided on an expansion board inserted into a computer or in an expansion unit connected to the computer and then causing a CPU or the like provided on the expansion board or in the expansion unit to perform a part or all of the actual operations based on instructions of the program code.

What is claimed is:

1. A substrate surface inspecting method of detecting a foreign matter attached to a substrate surface in a substrate processing system having a substrate processing apparatus that carries out predetermined processing on a substrate, the substrate surface inspecting method comprising:
   a fluid supply step of supplying onto a surface of the substrate a fluid containing an altering substance that alters a substance constituting the substrate that is exposed at the surface of the substrate;
   a surface altering step of altering the substance constituting the substrate around the attached foreign matter so as to emphasize the presence of the attached foreign matter; and a substrate surface inspecting step of inspecting the surface of the substrate onto which the fluid has been supplied.

2. A substrate surface inspecting method as claimed in claim 1, further having a substrate leaving step of, after the fluid has been supplied onto the surface of the substrate, leaving the substrate for a predetermined time period.

3. A substrate surface inspecting method of detecting a foreign matter attached to a substrate surface in a substrate processing system having a substrate processing apparatus that carries out predetermined processing on a substrate, the substrate surface inspecting method comprising:

a surface etching step of etching a surface of the substrate;

a projection forming step of etching the surface of the substrate except a part to which the foreign matter is attached and thereby forming a projection having the attached foreign matter on top thereof so as to emphasize the presence of the attached foreign matter; and a substrate surface inspecting step of inspecting the surface of the substrate of which the surface has been etched.

4. A substrate surface inspecting method of detecting a foreign matter attached to a substrate surface in a substrate processing system having a substrate processing apparatus that carries out predetermined processing on a substrate, the substrate surface inspecting method comprising:

an exposing step of exposing to light a photosensitive substance that has been applied onto a surface of the substrate;

a projection forming step including exposing to light the photosensitive substance applied onto the surface of the substrate except a part to which the foreign matter is attached so as to change a chemical structure thereof to be dissolvable by a predetermined solution, and dissolving and removing the exposed photosensitive substance, thereby forming a projection having the attached foreign matter on top thereof so as to emphasize the presence of the attached foreign matter; and a substrate surface inspecting step of inspecting the surface of the substrate on which the photosensitive substance has been developed.

5. A substrate surface inspecting method of detecting a foreign matter attached to a substrate surface in a substrate processing system having a substrate processing apparatus that carries out predetermined processing on a substrate, the substrate surface inspecting method comprising:

a pressure reducing step of reducing a pressure in a housing chamber housing the substrate;

a fluid supply step of supplying onto a surface of the substrate a fluid containing a reactive substance that reacts with water to form a solid;

a solid forming step of reacting water, which has been frozen around the attached foreign matter via cooling due to adiabatic expansion in said pressure reducing step, with the reactive substance and thereby forming a solid so as to emphasize the presence of the attached foreign matter; and a substrate surface inspecting step of inspecting the surface of the substrate onto which the fluid has been supplied.

6. A substrate surface inspecting method of detecting a foreign matter attached to a substrate surface in a substrate processing system having a substrate processing apparatus that carries out predetermined processing on a substrate, the substrate surface inspecting method comprising:

a rapid cooling step of rapidly cooling the substrate;

a fluid supply step of supplying onto a surface of the substrate a fluid containing a reactive substance that reacts with water to form a solid;

a solid forming step of reacting water, which has collected around the attached matter in said rapid cooling step, with the reactive substance and thereby forming a solid so as to emphasize the presence of the attached foreign matter; and a substrate surface inspecting step of inspecting the surface of the substrate onto which the fluid has been supplied.

* * * * *

UNITED STATES PATENT AND TRADEMARK OFFICE
CERTIFICATE OF CORRECTION

PATENT NO. : 7,976,637 B2
APPLICATION NO. : 11/683164
DATED : July 12, 2011
INVENTOR(S) : Hiroshi Nagaike et al.

Page 1 of 1

It is certified that error appears in the above-identified patent and that said Letters Patent is hereby corrected as shown below:

IN THE SPECIFICATIONS:

Column 15, line 30, delete "(IPA は、isopropyl alchol ではないでしょうか？ご確認ください)"

Signed and Sealed this
Thirteenth Day of September, 2011

David J. Kappos
*Director of the United States Patent and Trademark Office*